United States Patent
Fujii et al.

(10) Patent No.: US 10,499,978 B2
(45) Date of Patent: Dec. 10, 2019

(54) DISSECTING DEVICE AND DISSECTING SYSTEM

(71) Applicant: TERUMO KABUSHIKI KAISHA, Shibuya-ku, Tokyo (JP)

(72) Inventors: Tatsunori Fujii, Kanagawa (JP); Akihiro Takahashi, Kanagawa (JP); Makoto Jinno, Tokyo (JP)

(73) Assignee: TERUMO KABUSHIKI KAISHA, Shibuya-Ku, Tokyo (JP)

( * ) Notice: Subject to any disclaimer, the term of this patent is extended or adjusted under 35 U.S.C. 154(b) by 362 days.

(21) Appl. No.: 15/443,628

(22) Filed: Feb. 27, 2017

(65) Prior Publication Data
US 2017/0245922 A1  Aug. 31, 2017

(30) Foreign Application Priority Data

Feb. 29, 2016 (JP) .................................. 2016-038110

(51) Int. Cl.
*A61B 18/14* (2006.01)
*A61B 1/00* (2006.01)
(Continued)

(52) U.S. Cl.
CPC ...... *A61B 18/1445* (2013.01); *A61B 1/00087* (2013.01); *A61B 1/00195* (2013.01); *A61B 1/0661* (2013.01); *A61B 17/00008* (2013.01); *A61B 17/295* (2013.01); *A61B 17/320016* (2013.01); *A61B 18/1206* (2013.01);
(Continued)

(58) Field of Classification Search
CPC ............ A61B 17/00008; A61B 17/295; A61B 17/320016; A61B 18/1206; A61B 18/1445; A61B 18/1482; A61B 1/00087; A61B 1/00096; A61B 1/00195; A61B 1/0661; A61B 1/3137; A61B 2017/00778; A61B 2017/00969; A61B 2017/320052; A61B 2018/00428; A61B 2018/00589; A61B 2018/00595; A61B 2018/126; A61B 2018/1455; A61B 2018/1467
See application file for complete search history.

(56) References Cited

U.S. PATENT DOCUMENTS 5,658,282 A * 8/1997 Daw .................. A61B 18/1206
606/159
5,667,480 A * 9/1997 Knight .................. A61B 1/018
128/898

(Continued)

*Primary Examiner* — Michael F Peffley
(74) *Attorney, Agent, or Firm* — Buchanan Ingersoll & Rooney PC

(57) ABSTRACT

A dissecting device for dissecting tissue surrounding a blood vessel in a living body. The dissecting device includes a grasping section that includes an insertion lumen. The dissecting device includes a dissecting member at the distal portion of the grasping section. The dissecting member is insertable into the living body along the blood vessel to dissect the tissue surrounding the blood vessel in the living body. The dissecting member includes a treating section and a protruding section. The treating section performs a predetermined treatment of a branch vessel branching from the blood vessel. The protruding section protrudes from the treating section in the thickness direction of the treating section. The protruding section includes a guide section configured to guide the branch vessel toward the treating section.

7 Claims, 16 Drawing Sheets

(51) Int. Cl.
*A61B 1/06* (2006.01)
*A61B 17/295* (2006.01)
*A61B 17/32* (2006.01)
*A61B 18/12* (2006.01)
*A61B 17/00* (2006.01)
A61B 18/00 (2006.01)
A61B 1/313 (2006.01)

(52) U.S. Cl.
CPC ...... *A61B 18/1482* (2013.01); *A61B 1/00096* (2013.01); *A61B 1/3137* (2013.01); *A61B 2017/00778* (2013.01); *A61B 2017/00969* (2013.01); *A61B 2017/320052* (2013.01); *A61B 2018/00428* (2013.01); *A61B 2018/00589* (2013.01); *A61B 2018/00595* (2013.01); *A61B 2018/126* (2013.01); *A61B 2018/1455* (2013.01); *A61B 2018/1467* (2013.01)

(56) References Cited

U.S. PATENT DOCUMENTS

| | | | |
|---|---|---|---|
| 6,019,720 A * | 2/2000 | Bito | A61B 17/00008 600/104 |
| 6,193,653 B1 * | 2/2001 | Evans | A61B 17/00008 600/210 |
| 6,527,771 B1 * | 3/2003 | Weadock | A61B 17/00008 606/170 |
| 6,616,661 B2 * | 9/2003 | Wellman | A61B 18/1482 606/45 |
| 7,981,127 B2 | 7/2011 | Kasahara et al. | |
| 8,052,702 B2 * | 11/2011 | Hess | A61B 17/00008 600/104 |

* cited by examiner

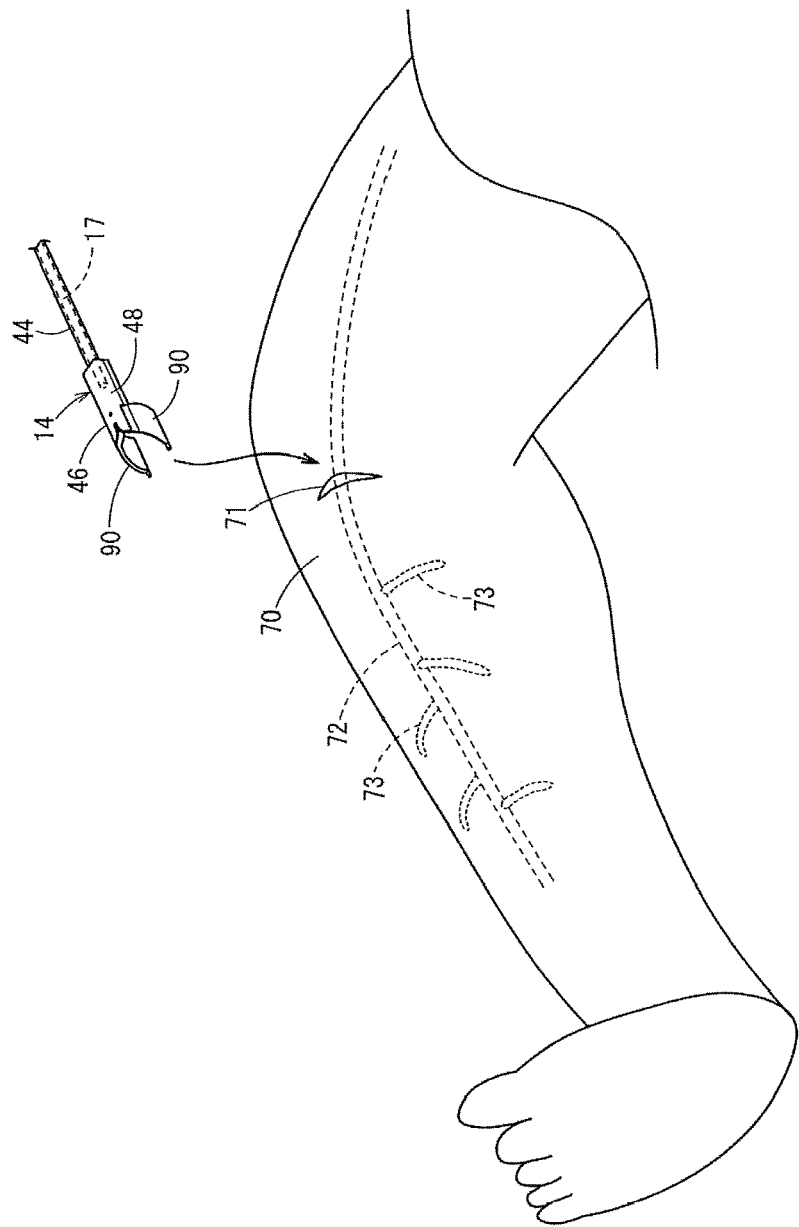

DISSECTING DEVICE AND DISSECTING SYSTEM

CROSS-REFERENCES TO RELATED APPLICATIONS

This application claims priority to Japanese Application No. 2016-038110 filed on Feb. 29, 2016, the entire content of which is incorporated herein by reference.

TECHNICAL FIELD

The present disclosure generally relates to a dissecting device, a dissecting system and a dissecting method for dissecting tissue such as fat in a living body.

BACKGROUND DISCUSSION

It is widely known to use an artery graft represented by internal thoracic artery, gastroepiploic artery and radial artery or a vein graft represented by great saphenous vein as a bypass vessel in performing vascular bypass grafting at the heart (coronary artery bypass grafting: CABG). It has also been reported that artery grafts (particularly, internal thoracic artery) offer higher long-term patency rates than vein grafts.

Vein grafts are commonly deemed to be poor in long-term patency rate. In recent years, however, it has been reported that the long-term patency rate concerning a vein graft is enhanced when the vein graft is harvested when being covered with the surrounding tissue (for example, fat, connective tissue, tissue between a skin layer and a muscle layer, tissue between a skin layer and an interosseous membrane, branch vessels, etc.) and is used as a bypass vessel while remaining covered with the tissue.

U.S. Pat. No. 7,981,127 discloses a system to endoscopically harvest a blood vessel in a living body.

In the system disclosed in U.S. Pat. No. 7,981,127, however, a blood vessel and the surrounding tissue (fat) are first dissected by a dissecting device (dissector 3), and then a branch vessel exposed in the living body is stanched and cut by a cutting device (treatment sheath 2). The system of U.S. Pat. No. 7,981,127 is not configured to enable a blood vessel to be harvested together with the surrounding tissue. This system additionally has a drawback in that the stanching and cutting may be conducted by capturing the branch vessel exposed in the living body, and, therefore, workability (i.e., operability) in harvesting the blood vessel is poor.

SUMMARY

The dissecting device, dissecting system, and dissecting method disclosed here permit a blood vessel to be harvested (i.e., extracted or removed from the living body) together with the surrounding tissue with good workability.

In one aspect, there is provided a dissecting device including: a grasping section which has an insertion lumen permitting an imaging device to be inserted therein and which is adapted to be graspable by a user; and a dissecting member which is provided at a distal portion of the grasping section and which, when inserted into a living body along a blood vessel, dissects tissue surrounding the blood vessel in the living body. In the dissecting device, the dissecting member includes a dissecting section provided with a treating section adapted to perform a predetermined treatment of a branch vessel branched from the blood vessel, and a protruding section protruding from the dissecting section in a thickness direction of the dissecting section, and the protruding section has a guide section adapted to guide the branch vessel toward the treating section.

The dissecting device can bring branch vessels near and guide the branch vessels to the treating section by the guide section provided in the protruding section protruding from the dissecting section, when the dissecting member moves forward (advances) within the living body. In other words, a capture range for the branch vessels can be widened by including the guide section. Consequently, branch vessels that cannot be successfully captured by the dissecting section alone can be captured and efficiently treated by the treating section. The treatment of the captured branch vessels can be easily carried out while observing the branch vessels via the imaging device inserted in the insertion lumen.

In the dissecting device, two protruding sections may be provided to be spaced apart in a width direction of the dissecting section.

This configuration makes it possible to further broaden the capture range for branch vessels.

In the dissecting device, the two protruding sections may be curved to bulge toward an outside in the width direction of the dissecting section.

This configuration makes it possible to further widen the capture range for branch vessels.

In the dissecting device, the protruding section may be curved to be displaced toward an inside in a width direction of the dissecting section in going in a direction in which the protruding section protrudes from the dissecting section (i.e., a pair of projecting portions curve toward the center axis of the dissecting device in the width direction of the dissecting device from the proximal end of the projecting portions to the distal end of the projecting portions).

This configuration makes it possible to smoothly guide the branch vessels.

In the dissecting device, a portion of the guide section on a protruding end side of the protruding section may be located on a distal side relative to a portion of the guide section on a base side of the protruding section.

A branch vessel can be gradually brought toward the dissecting section side based on this configuration when the dissecting member moves forward within the living body. Therefore, the branch vessels can be guided more smoothly.

In the dissecting device, the thickness of the protruding section may decrease in a direction toward the protruding end side of the protruding section.

Insertion resistance at the time of inserting the protruding section into tissue for disposing the dissecting member in the living body can thus be reduced.

In the dissecting device, the length in an axial direction of the protruding section may decrease toward the protruding end side of the protruding section.

The insertion resistance at the time of inserting the protruding section into tissue for disposing the dissecting member in the living body can thus be reduced.

In the dissecting device, the dissecting section may be formed such that its thickness increases in the direction toward a base end of the dissecting section, at least at part of the dissecting section.

This configuration enables effective dissection of tissue in a living body.

In the dissecting device, the dissecting section may have a blood vessel guide passage configured to guide the branch vessel toward the dissecting section.

This configuration enables the user to dissect the tissue (fat) in the living body and to easily capture the branch vessels embedded in the tissue when inserting the dissecting device into the living body along a blood vessel.

In another aspect, there is provided a dissecting system including: a first dissecting device having a first dissecting member which, when inserted into a living body along a blood vessel, dissects tissue surrounding the blood vessel in the living body; and a second dissecting device having a second dissecting member which, when inserted into the living body along the blood vessel, dissects the tissue in the living body. In the dissecting system, the first dissecting member includes a first dissecting section, two second dissecting sections which protrude in a thickness direction of the first dissecting section from both sides with respect to a width direction of the first dissecting section and which are provided with first guide sections adapted to guide a branch vessel branched from the blood vessel, and a first treating section adapted to perform a predetermined treatment of the branch vessel. In addition, the second dissecting member includes a dissecting section, two protruding sections which protrude in a thickness direction of the dissecting section from both sides with respect to a width direction of the dissecting section and which are provided with second guide sections adapted to guide the branch vessel, and a second treating section adapted to perform a predetermined treatment of the branch vessel.

According to the dissecting system, by dissecting tissue in a living body along a blood vessel by use of one of the first dissecting device and the second dissecting device and then dissecting the tissue in other part in the living body along the blood vessel by use of the other of the first dissecting member and the second dissecting member, the tissue can be dissected over the whole circumferential range of the perimeter of the blood vessel. Therefore, the blood vessel can be efficiently harvested from the living body together with the surrounding tissue.

In the dissecting system, the first guide sections and the second guide sections may be formed in such a manner that, when the tissue is dissected by the first dissecting device with the first dissecting section disposed on one side with respect to a radial direction of the blood vessel and the tissue is dissected by the second dissecting device with the dissecting section disposed on the other side with respect to the radial direction of the blood vessel, a capture range within which capture of the branch vessel by the first dissecting member is possible and a capture range within which capture of the branch vessel by the second dissecting member is possible overlap with each other in regard of the radial direction of the blood vessel.

This configuration helps ensure that when the tissue surrounding a blood vessel in a living body is dissected by sequentially using the first dissecting device and the second dissecting device, branch vessels that could not be successfully captured by the first-used device can be reliably captured by the secondly used device.

The dissecting system may have a configuration wherein when the tissue is dissected by one of the first dissecting device and the second dissecting device and thereafter the tissue is dissected by the other of the first dissecting device and the second dissecting device, the other device passes outside of a part where the one device has passed.

By this configuration, the tissue on the side of harvesting that has been dissected by the first-used device can be restrained from being damaged by the secondly used device.

In a further aspect, there is provided a dissecting method for dissecting tissue surrounding a blood vessel in a living body by use of a dissecting device. In the dissecting method, the dissecting device includes a grasping section which has an insertion lumen permitting an imaging device to be inserted therein and which is adapted to be graspable by a user, and a dissecting member which is provided at a distal portion of the grasping section and which, when inserted into the living body along the blood vessel, dissects the tissue surrounding the blood vessel in the living body. The dissecting member includes a dissecting section, two protruding sections which protrude from the dissecting section in a thickness direction of the dissecting section and which are provided with guide sections adapted to guide a branch vessel toward the dissecting section, and a treating section adapted to perform a predetermined treatment of the branch vessel. The dissecting method includes: inserting the two protruding sections into the tissue in such a manner that the blood vessel is disposed between the two protruding sections, via an incision formed in a skin; reversing the dissecting member around the blood vessel, after the inserting; and moving the dissecting device forward along the blood vessel, after the reversing.

According to the dissecting method, the branch vessels that cannot be successfully captured by the dissecting section alone can be captured, by drawing the branch vessels near by the guide sections provided in the two protruding sections protruding from the dissecting section, attendant on the forward movement of the dissecting member within the living body. Besides, in this dissecting method, dissection by the dissecting device is started after the dissecting member is inserted into the living body while avoiding the blood vessel in the insertion step and the dissecting member is reversed in the reversion step. Therefore, notwithstanding the two protruding sections are provided, the tissue on the deeper part side in the living body as compared to the blood vessel can be dissected without any trouble.

In yet another aspect, there is provided a dissecting method for dissecting tissue surrounding a blood vessel in a living body, by use of a first dissecting device having a first dissecting member which, when inserted into the living body along the blood vessel, dissects the tissue surrounding the blood vessel in the living body, and a second dissecting device having a second dissecting member which, when inserted into the living body along the blood vessel, dissects the tissue in the living body. In the dissecting method, the first dissecting member includes a first dissecting section, two second dissecting sections which protrude in a thickness direction of the first dissecting section from both sides with respect to a width direction of the first dissecting section and which are provided with first guide sections adapted to guide a branch vessel branched from the blood vessel, and a first treating section adapted to perform a predetermined treatment of the branch vessel. In addition, the second dissecting member includes a dissecting section, two protruding sections which protrude in a thickness direction of the dissecting section from both sides with respect to a width direction of the dissecting section and which are provided with second guide sections adapted to guide the branch vessel, and a second treating section adapted to perform a predetermined treatment of the branch vessel. The dissecting method includes a first dissecting step of dissecting the tissue by one of the first dissecting device and the second dissecting device, and a second dissecting step of dissecting the tissue by the other of the first dissecting device and the second dissecting device after the first dissecting step.

According to the dissecting method, tissue surrounding a blood vessel in a living body can be dissected by sequentially using the first dissecting device and the second dissecting device. Therefore, the blood vessel can be efficiently harvested from the living body together with the surrounding tissue.

In the dissecting method, a configuration may be adopted wherein in the step of using the first dissecting device of the first dissecting step and the second dissecting step, the first dissecting device is moved forward with the first dissecting section disposed on one side with respect to a radial direction of the blood vessel, whereas in the step of using the second dissecting device of the first dissecting step and the second dissecting step, the second dissecting device is moved forward with the dissecting section disposed on the other side with respect to the radial direction of the blood vessel, and a capture range within which capture of the branch vessels is possible in the second dissecting step and a capture range within which capture of the branch vessels is possible in the first dissecting step overlap with each other, in regard of the radial direction of the blood vessel.

By this configuration, the branch vessels that cannot be successfully captured by the device used in the first dissecting step can be reliably captured by the device used in the second dissecting step.

In the dissecting method as above, in the second dissecting step, the other device may pass outside of a part where the one device has passed in the first dissecting step.

By this configuration, the tissue on the side of harvesting that has been dissected in the first dissecting step can be restrained from being damaged by the device used in the second dissecting step.

A dissecting device is also disclosed for dissecting tissue surrounding a blood vessel in a living body. The dissecting device includes a grasping section that includes an insertion lumen. The dissecting device includes a dissecting member at the distal portion of the grasping section. The dissecting member is insertable into the living body along the blood vessel to dissect the tissue surrounding the blood vessel in the living body. The dissecting member includes a treating section and a protruding section. The treating section performs a predetermined treatment of a branch vessel branching from the blood vessel. The protruding section protrudes from the treating section in the thickness direction of the treating section. The protruding section includes a guide section configured to guide the branch vessel toward the treating section.

The disclosure also involves a dissecting system including a first dissecting device insertable into a living body and movable along a blood vessel and a second dissecting device insertable into the living body and movable along the blood vessel. The first dissecting device includes a first dissecting member configured to dissect tissue surrounding the blood vessel in the living body when the first dissecting member moves forward along the blood vessel in the living body. The first dissecting member includes a first dissecting section, two second dissecting sections, and a first treating section. The first dissecting section extends in an axial direction and possesses a thickness direction and a width direction. The first dissecting section possesses a first lateral side and a second lateral side opposite the first lateral surface in the width direction. One of the two second dissecting sections protrudes downward in the thickness direction of the first dissecting section from the first lateral side of the first dissecting section and the other of the two second dissecting sections protrudes downward in the thickness direction of the first dissecting section from the second lateral side of the first dissecting section. The two second dissecting sections include first guide sections configured to guide a branch vessel branched from the blood vessel to the first treating section. The first treating section is configured to perform a predetermined treatment of the branch vessel when the first guide sections guide the branch vessel to the first treating section. The second dissecting device includes a second dissecting member configured to dissect the tissue surrounding the blood vessel in the living body when the second dissecting member moves forward along the blood vessel in the living body. The second dissecting member includes a dissecting section, two protruding sections, and a second treating section. The two protruding sections protrude upward in the thickness direction of the dissecting section from both sides of the dissecting section in the width direction. The two protruding sections include second guide sections configured to guide the branch vessel to the second treating section. The second treating section is configured to perform the predetermined treatment of the branch vessel.

In another aspect, this disclosure relates to a dissecting method for dissecting tissue surrounding a blood vessel in a living body using a dissecting device. The method includes introducing the dissecting device into the living body by way of an incision. The dissecting device includes a main body and two protruding portions. The main body possesses a thickness direction, and the two protruding portions protruding beyond the main body in the thickness direction of the main body in a first direction during the introducing of the dissecting device into the living body. The method also includes rotating the dissecting device to a rotated position while the dissecting device is in the living body so that the protruding portions protrude beyond the main body in the thickness direction of the main body in a second direction. The second direction is diametrically opposite the first direction. The method includes dissecting the tissue surrounding the blood vessel in the living body by moving the dissecting device forward along the blood vessel while the dissecting device is in the rotated position.

In accordance with the dissecting device and the dissecting system of the present disclosure, branch vessels can be captured in a widened range, and a blood vessel can be harvested with excellent workability.

BRIEF DESCRIPTION OF THE DRAWINGS

FIG. 12 illustrates a method of inserting the second dissecting device into a living body.

DETAILED DESCRIPTION

Set forth below with reference to the accompanying drawings is a detailed description of embodiments of a dissecting device, a dissecting system and a dissecting method representing examples of the inventive dissecting device, dissecting system and dissecting method disclosed here.

[General Configuration of Dissecting System 10]

Figure 1:
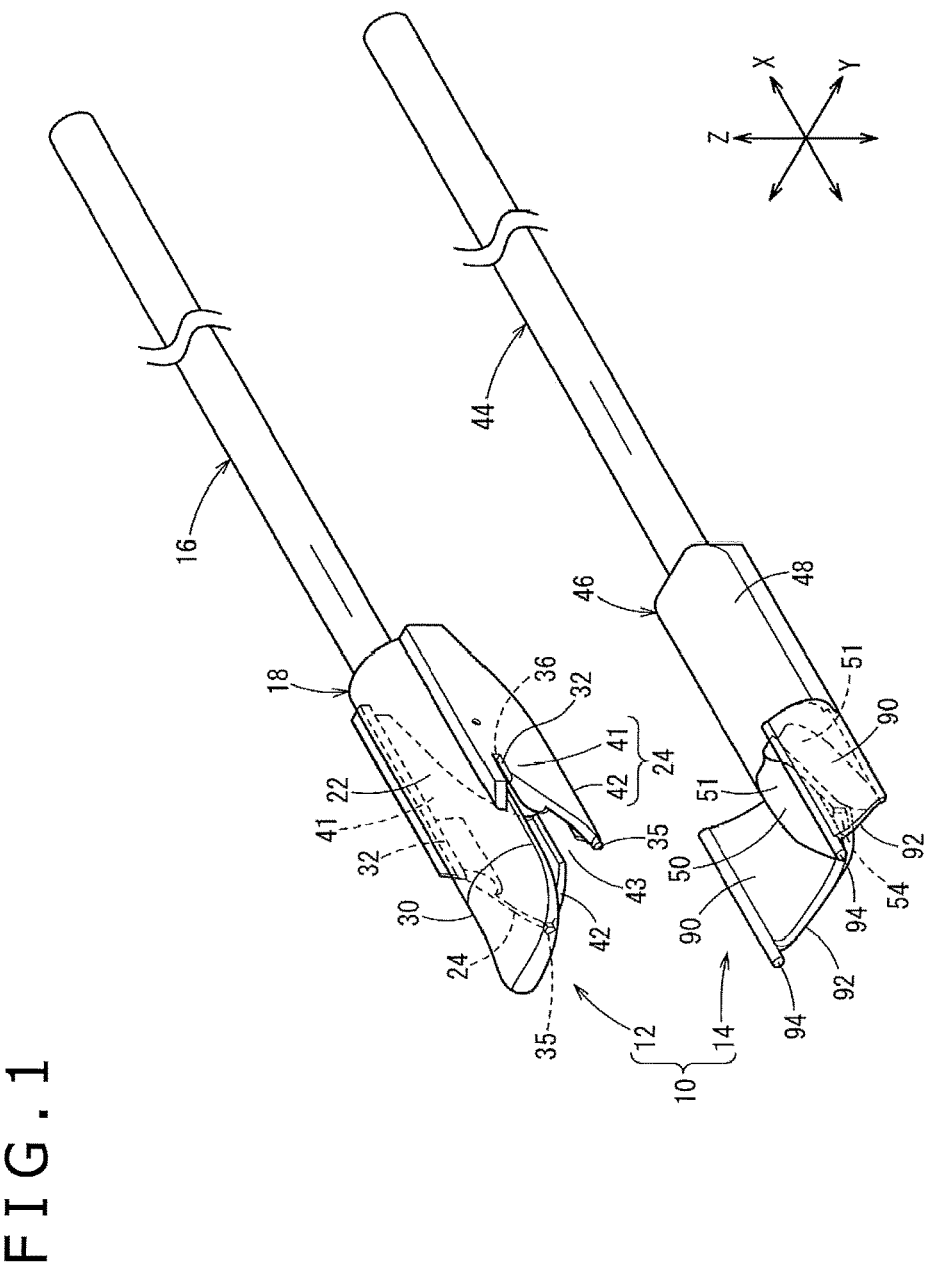
FIG. 1 is a perspective view of a dissecting system.

A dissecting system 10 shown in FIG. 1 is a device used to harvest a blood vessel for use as a bypass vessel in carrying out vascular bypass grafting (particularly, coronary artery bypass grafting: CABG). The dissecting system 10 can harvest a blood vessel when the blood vessel is covered with surrounding tissue (fat, connective tissue, etc.). The blood vessel to be harvested using the dissecting system 10 is not particularly limited so long as it is a blood vessel that can be used as a bypass vessel. Examples of an applicable blood vessel include internal thoracic artery, gastroepiploic artery, radial artery, and saphenous veins (great saphenous vein and small saphenous vein).

In a preferred embodiment the harvested blood vessel is a saphenous vein. The use of the dissecting system 10 facilitates harvesting of a blood vessel in the state in which the blood vessel is covered with the surrounding tissue. When a saphenous vein is harvested by use of the dissecting system 10 and is used as a bypass vessel, an enhanced long-term patency rate is obtained after the bypass grafting.

The dissecting system 10 includes two kinds of dissecting devices 12 and 14. Hereinafter, one of the two dissecting devices 12 and 14 will be referred to as "the first dissecting device 12," and the other 14 as "the second dissecting device 14." Both the first dissecting device 12 and the second dissecting device 14 are an elongated device to be inserted into a living body along a blood vessel such as a saphenous vein.

[Configuration of First Dissecting Device 12]

Figure 2:
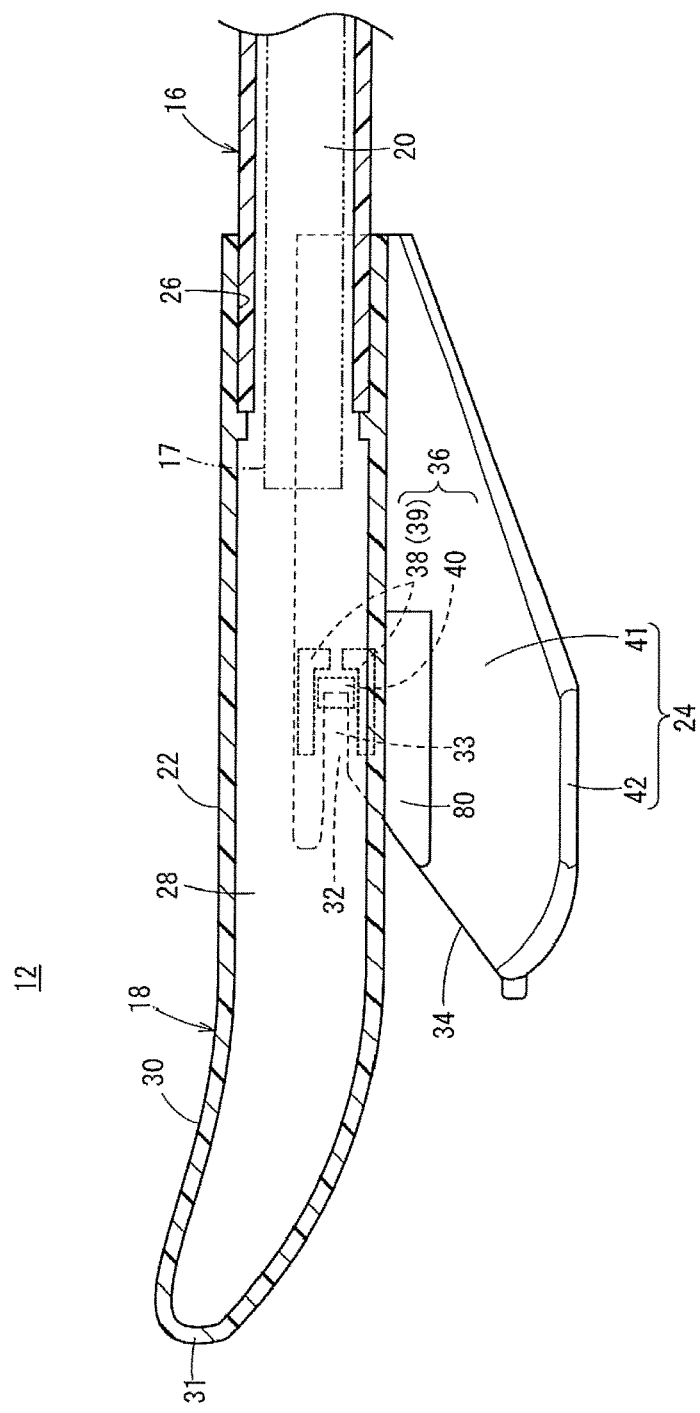
FIG. 2 is a sectional view of a distal portion of a first dissecting device.

The first dissecting device 12 includes a grasping section 16 adapted (configured) to be graspable by a user (e.g., a technician or an operator), and a dissecting member 18 (first dissecting member) provided at a distal portion of the grasping section 16. As depicted in FIG. 2, the grasping section 16 is a tubular member (e.g., a cylindrical body) possessing an insertion lumen 20 in which an imaging device 17 (for example, an endoscope) can be inserted. The grasping section 16 in the illustrated example is formed in a rectilinear shape. Examples of materials of the grasping section 16 include rigid resins and metals.

The insertion lumen 20 is a through-hole which extends along a longitudinal direction of the grasping section 16. The insertion lumen 20 opens at a distal surface and a proximal surface of the grasping section 16 (i.e., the distal-most end and the proximal-most end of the insertion lumen 20 are open). An objective lens and an illuminating portion, for example, may be located at the distal portion of the imaging device 17.

The dissecting member 18 illustrated in FIG. 1 includes a hollow-structured base section 22 (first dissecting section) which is fixed to a distal portion of the grasping section 16. The dissecting member 18 also includes a pair of side sections 24 (second dissecting section) projecting from both sides in a width direction of the base section 22. The pair of side sections 24 also project toward one side (i.e., the lower side in FIG. 1; a first direction) in a thickness direction of the base section 22. The base section 22 has a flattened cross-sectional shape which is short in the vertical direction and long in the width direction (i.e., the length of the base section 22 in the width direction is greater than the length of the base section 22 in the vertical direction). The width of the base section 22 is greater than the outside diameter of a blood vessel to be harvested (i.e., the target blood vessel).

"The thickness direction" in regard to the dissecting member 18 and the base section 22 refers to a height direction (i.e., the Z-direction in FIG. 1) perpendicular to the axial direction (i.e., the X-direction in FIG. 1). The axial direction is the longitudinal direction of the first dissecting device 12 in FIG. 1. "The width direction" in regard to the dissecting member 18 and the base section 22 refers to a direction (i.e., the Y-direction in FIG. 1) perpendicular to the axial direction (X-direction) and the height direction (Z-direction) of the dissecting member 18 in FIG. 1.

As shown in FIG. 2, the base section 22 includes a fixing hole 26 in which a distal portion of the grasping section 16 is fixed (i.e., attached or connected). The base section 22 also includes a cavity 28 which extends from a position slightly distal of the fixing hole 26 to the vicinity of the distal end of the base section 22. The cavity 28 communicates with the insertion lumen 20.

The base section 22 possesses a distal dissecting section 30 at the distal portion of the base section 22, which dissects tissue. The distal dissecting section 30 is tapered distally (i.e., the outer diameter of the distal dissecting section 30 decreases towards the distal-most end of the base section 22), for easy dissection of tissue. Specifically, the distal dissecting section 30 is formed in such a shape that the length in a minor axis direction and the length in a major axis direction of its cross-sectional shape gradually decrease in the distal direction (i.e., towards the distal end 31 of the distal dissecting section 30). A distal end 31 (apex portion or distal-most end) of the distal dissecting section 30 possesses a rounded shape to prevent the distal dissecting section 30 from damaging a blood vessel to be harvested or branch vessels. The distal dissecting section 30 is also curved such that the distal dissecting section 30 gradually extends upward from a base portion located on the proximal side of the distal dissecting section 30 (i.e., the distal dissecting section 30 curves upwards relative to the grasping section 16).

The base section 22 is formed of a transparent (light-transmitting) material (for example, glass, transparent resin or the like). With the imaging device 17 inserted in the insertion lumen 20 and the cavity 28, it is possible to image the front side and the surroundings of the base section 22 for observation (visual confirmation) by the imaging device 17. The base section 22 preferably is substantially colorless and transparent, but the base section 22 may be colored as long as it is transparent.

The pair of side sections 24 are members for dissecting tissue on both lateral sides under the base section 22. The pair of side sections 24 are provided at near-proximal-end portions on both lateral sides of the base section 22. Therefore, the base section 22 (which includes the distal dissecting section 30) protrudes distally beyond the pair of side sections 24. The base section 22 extends (e.g., warps or bends) gently (gradually) upward on the distal side of the pair of side sections 24. The pair of side sections 24 are located on proximal to the upward-extending portion of the base section 22.

As illustrated in FIG. 1, each of the pair of side sections 24 is provided with a groove section 32 into which a branch vessel 73 (see FIG. 3, etc.) branched from a blood vessel 72 can be accepted. Each of the pair of side sections 24 also includes a guide section 34 which is continuous with a distal end of the groove section 32. The guide section 34 guides the branch vessel 73 into the groove section 32. Each of the pair of side sections 24 includes a distal projection 35 projecting distally from a distal end of the guide section 34. The groove section 32 shown as an example in FIG. 1 is a rectilinear groove that extends along a longitudinal direction of the dissecting member 18, opens in the distal direction, and penetrates the side section 24 in a thickness direction of the side section 24 (the width direction of the base section 22). The width (the dimension measured in the height direction of the dissecting member 18) of the groove section 32 may be constant along the lengthwise direction of the groove section 32 or may gradually decrease in the proximal direction (i.e., taper towards the proximal-most end of the groove section 32).

A treating section 36 (first treating section) for stanching and cutting the branch vessel 73 is provided at the groove section 32 as illustrated in FIG. 2. The treating section 36 includes a stanching section 38 for stanching the branch vessel 73, and a cutting section 40 (cutting edge or cutting surface) for cutting the branch vessel 73. The stanching section 38 has a bipolar structure including a pair of electrodes 39. The pair of electrodes 39 are provided respectively on both sides in the width direction of the groove section 32.

When a branch vessel 73 is guided into the groove section 32, the branch vessel 73 can be stanched by thermal coagulation by applying a high-frequency voltage to the pair of electrodes 39. The cutting section 40 is provided proximally of the distal ends of the pair of electrodes 39. The branch vessel 73 can be cut by the cutting section 40 after the branch vessel 73 has undergone thermal coagulation based on this configuration. At least part of the groove section 32 thus includes a treatment region 33 where a predetermined treatment (e.g., stanching and cutting) is performed on the branch vessel 73 by the action of the treating section 36.

Figure 3:
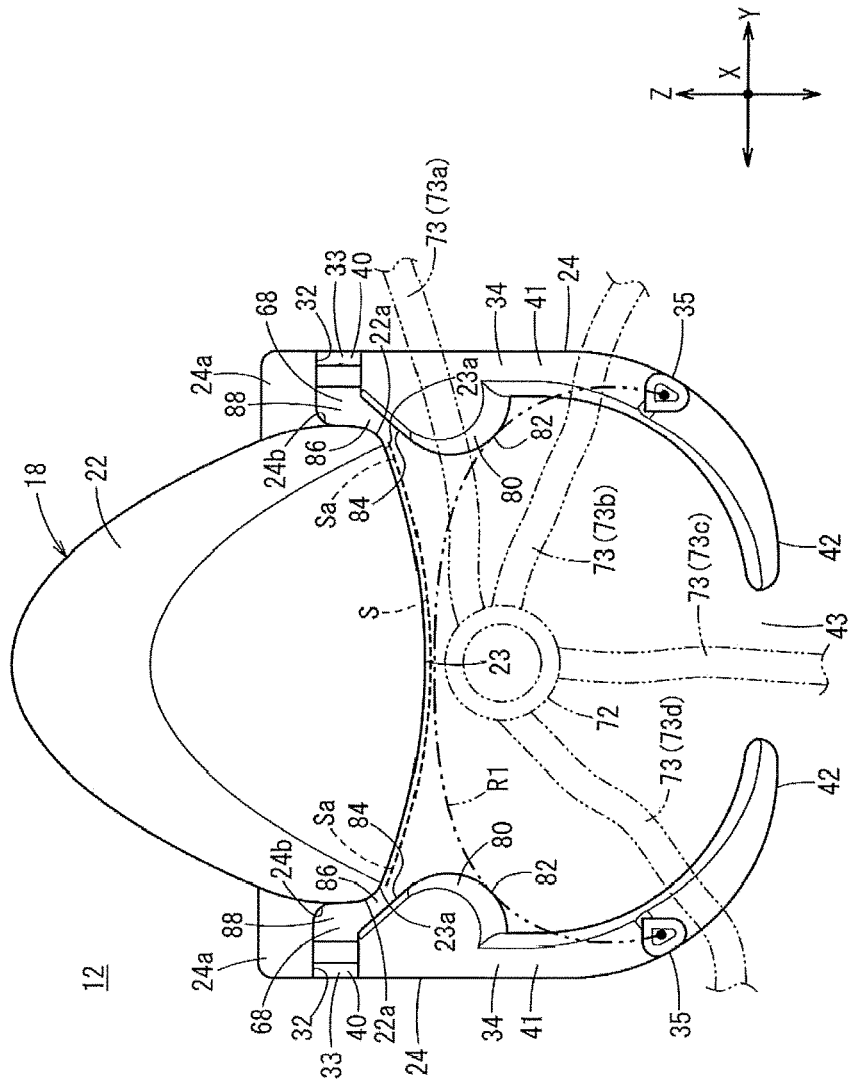
FIG. 3 is a front view of the first dissecting device.

When the dissecting member 18 moves forward within a living body as illustrated in FIG. 3, the base section 22 dissects tissue in the thickness direction of the base section 22 (the direction of alignment of the base section 22 with the blood vessel 72). A dissection interface S between the blood vessel 72 and the base section 22 is formed along a bottom portion 23 (bottom surface) of the base section 22. Portions of the dissection interface S on the side section 24 sides are formed by those corner portions 23a of the bottom portion 23 which are on the side section 24 sides. Hereinafter, those portions of the dissection interface S which are formed by the corner portions 23a are referred to as "the dissection interfaces Sa."

The treatment region 33 of the groove section 32 is configured so that a space 68 is formed between the treatment region 33 and the base section 22. Tissue (fat 74) is inhibited from entering the space 68 between the treatment region 33 and the base section 22 at the time of dissection of tissue by the dissecting member 18. A distal end of the space 68 is located at the same position as a distal opening of the groove section 32 in the X-direction (i.e., the longitudinal direction). The proximal end of the space 68 is located at the same position as, or proximal to, the proximal end of the treatment region 33 in the X-direction (i.e., the longitudinal direction). The space 68 is a groove adjacent to the groove section 32. The space 68 is a groove defined between the base section 22 and the side section 24. The distal end of the space 68 may communicate with a first slit 86 which is described below. When the distal end of the space 68 communicates with the first slit 86, the space 68 is formed between the first slit 86 (described below) and the treatment region 33. The space 68 is disposed between a base portion 24a of the side section 24 extending from the base section 22 and the corner portion 23a of the bottom portion 23 (bottom surface) of the base section 22 in the Z-direction. The space 68 is located on the upper side (on the side of the base portion 24a of the side section 24) relative to the dissection interface Sa. When a pressing section 80 is included, the space 68 is disposed between the base portion 24a of the side section 24 and the pressing section 80 in the X-direction. The bottom portion 23 (bottom surface) of the base section 22 is configured such that a lower end of the groove portion 32 is located at the same position as, or on the upper side (the base portion 24a side) of, the corner portion 23a forming the dissection interface Sa in the Z-direction. The space 68 is configured such that the slit width (Z-direction) of the first slit 86 is greater than the groove width (Z-direction) of the groove section 32 from the treatment region 33 to the distal opening of the groove section 32. The space 68 is surrounded by the bottom portion 23 (bottom surface) of the base section 22, a side wall of the base section 22, and an opening of the side section 24, in the Y-direction. The first slit 86 is a groove possessing a slit width in the Y-direction that is narrower than the width of the space 68 in the Z-direction. The space 68 is adjacent to, and communicates with, the treatment region 33. The distal end of the space 68 is located distal to the distal end of the treatment region 33 in the X-direction. The proximal end of the space 68 is located at the same position as, or proximal to, the proximal end of the treatment region 33. The dissecting member 18 has wall portions that form (provide) the spaces 68. The wall portions illustrated in FIG. 3 are the corner portions 23a of the bottom portion 23, and the treatment regions 33 are located on the upper side (a direction opposite to the direction of protrusion of the side sections 24 from the base section 22; a second direction) relative to the corner portions 23a. The treatment regions 33 are thus located above the dissection interfaces Sa formed by the corner portions 23a. The narrow groove may be formed by a rectilinear portion of the pressing section 80 (described below) and a curved portion of the wall portion. When the pressing section 80 is curved, the narrow groove may be the space 68 between a curved portion of the wall portion and a curved portion of the pressing section 80. In addition, one or both of the curved portion of the wall portion and the curved portion of the pressing section 80 may be curved toward the inner side (i.e., toward the center of dissecting member 18). A wall surface of the base portion 24a of the side section 24 defining a second slit 88 (described below) may have a curved surface 24b which is curved in an arcuate shape extending from a side wall of the base section 22 toward the groove section 32. The branch vessel 73 introduced into the space 68 can be smoothly guided by the curved surface 24b into the groove section 32. A corner portion 22a of the base section 22 that is continuously ranging (extending) from the corner portion 23a of the bottom portion 23 to the side wall is curved in an arcuate shape. An S-shaped wall surface is created by the arcuate-curved corner portion 22a of the base section 22, the side wall of the base section 22, and the above-mentioned curved surface 24b. The S-shaped wall surface helps enable the branch vessel 73 to be smoothly guided into the groove section 32. When the dissecting member 18 includes the pressing section 80, the curved corner portion 22a of the base section 22 protrudes toward the pressing section 80, and the above-mentioned S-shaped wall surface is opposite the pressing section 80. In the case where the pressing section 80 is provided, the first slit 86 (described below) is configured such that its slit width is narrowest at the location of the arcuate-curved corner portion 22a of the base section 22, its slit width is wider at the location on the groove section 32 side of the corner portion 22a than at the location of the corner portion 22a, and its slit width is wider at the location on the opposite side of the corner portion 22a from the groove section 32 than at the location of the corner portion 22a.

FIG. 3 shows that the groove section 32 is entirely disposed above the corner portion 23a. However, if the part of the groove section 32 which has the treatment region 33 is above the corner portion 23a (for example, as shown as an example in FIGS. 4A to 4C), the other part of the groove section 32 may be disposed below the corner portion 23a.

Figure 4A:
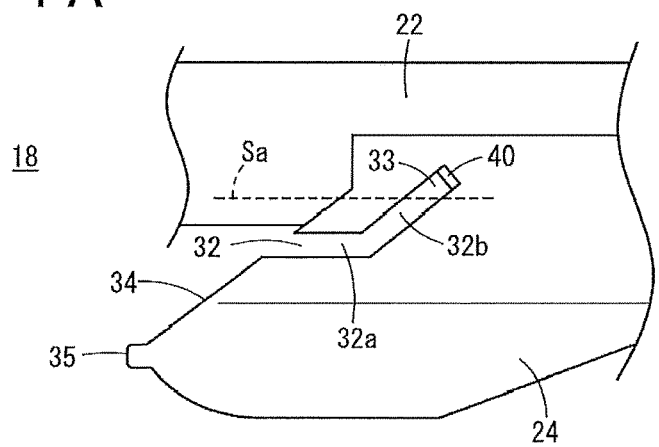
FIG. 4A is a side view showing a first modification of a groove section of the first dissecting device.

A groove section 32 embodiment depicted in FIG. 4A includes a parallel portion 32a parallel to the axial direction of the first dissecting device 12 that opens in the distal direction (i.e., the distal end of the parallel portion 32a is open), and an inclined portion 32b inclined relative to the parallel portion 32a. The treatment region 33 is provided at a proximal portion of the inclined portion 32b. The treatment region 33 is located above the corner portion 23a. The treatment region 33 is thus located above the dissection interface Sa.

Figure 4B:
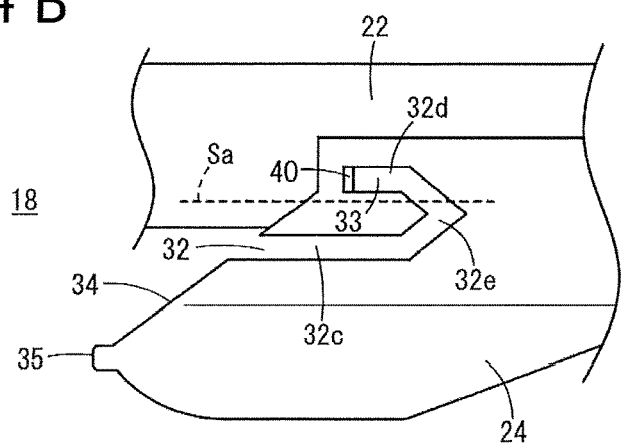
FIG. 4B is a side view showing a second modification of the groove section of the first dissecting device.

A groove section 32 embodiment illustrated in FIG. 4B includes a first parallel portion 32c parallel to the axial direction of the first dissecting device 12 that opens in the distal direction (i.e., the distal end of the parallel portion 32a is open), a second parallel portion 32d which extends above the first parallel portion 32c parallel to the axial direction and is provided with the treatment region 33, and a turning-back portion 32e which interconnects the first parallel portion 32c and the second parallel portion 32d. The treatment region 33 in the second parallel portion 32d is located above the corner portion 23a. The treatment region 33 is thus located above the dissection interface Sa.

Figure 4C:
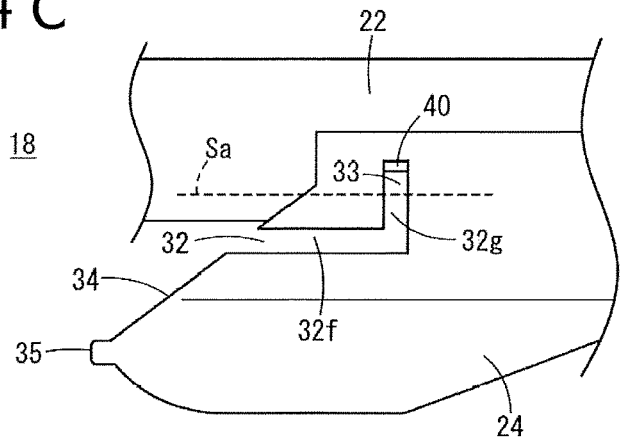
FIG. 4C is a side view showing a third modification of the groove section of the first dissecting device.

A groove section 32 embodiment shown in FIG. 4C includes a parallel portion 32f parallel to the axial direction of the first dissecting device 12 that opens in the distal direction, and a vertical portion 32g extending vertically upward from the proximal end of the parallel portion 32f. The treatment region 33 is provided at an upper end portion of the vertical portion 32g as shown in FIG. 4C. The treatment region 33 is located above the corner portion 23a. The treatment region 33 is thus located above the dissection interface Sa.

As illustrated in FIG. 2, the guide section 34 is inclined toward the groove section 32 side, at a distal portion of the side section 24. Specifically, the guide section 34 is inclined towards the base section 22 side from the distal end to the proximal end of the guide section 34. The distal projection 35 is at a protruding end of the guide section 34. The guide section 34 and the distal projection 35 configured as described above help ensure that when the dissecting member 18 is moved forward along a blood vessel 72 (i.e., a blood vessel to be harvested), a branch vessel 73 that comes into contact with the distal projection 35 or the guide section 34 can be lifted up and smoothly guided toward the groove section 32 side.

As indicated by imaginary lines in FIG. 3, the dissecting member 18 has a capture range R1 between the distal projections 35 and the base section 22. Capture of the branch vessels 73 by the pair of guide sections 34 is possible within the capture range R1. Branch vessels 73a and 73b shown in FIG. 3 fall within the capture range R1 and are, therefore, guided into the groove section 32 by the side section 24 when the dissecting member 18 is moved forward along the blood vessel 72. On the other hand, branch vessels 73c and 73d fall outside of the capture range R1 and, therefore, are not guided into the groove section 32. These branch vessels 73c and 73d instead pass between a pair of projecting portions 42 (described below) when the dissecting member 18 is advanced along the blood vessel 72.

Each of the pair of side sections 24 includes a side wall portion 41 extending from the base section 22, and the projecting portion 42 projecting from the side wall portion 41 toward the inner side (i.e., toward the center of the dissecting member 18 in the width direction) opposite the base section 22. The groove section 32 and the guide section 34 described above are provided in the side wall portion 41. The pair of projecting portions 42 are opposite each other. The thickness of the pair of projecting portions 42 is smaller than the thickness of the base section 22. Each projecting portion 42 has a thickness which decreases from the side wall portion 41 side toward a projecting end of the projecting portion 42. Each projecting portion 42 may also be constant in thickness, from the side wall portion 41 side toward the projecting end of the projecting portion 42. As illustrated in the FIG. 3 front view of the dissecting member 18, each projecting portion 42 is curved in an arcuate shape from the side wall portion 41 (i.e., each projecting portion 42 curves towards the center of the dissecting member 18 from the side wall portion 41 as shown in FIG. 3). Each projecting portion 42 may be rectilinear in shape as shown in FIG. 3.

The projecting ends of the pair of projecting portions 42 face each other. A space 43 is between the pair of projecting portions 42 to permit the branch vessel 73 to pass therethrough. The tissue located on the opposite side of the blood vessel 72 from the base section 22 (excluding the portion of the tissue located in the space 43) can be dissected by the projecting portions 42 when the dissecting member 18 is moved forward along the blood vessel 72 to be harvested.

Each of the pair of side sections 24 illustrated in FIG. 3 includes the pressing section 80 which presses the branch vessel 73 toward the base section 22 side when the dissecting member 18 is moved forward in the living body. Specifically, the dissecting member 18 has a pair of pressing sections 80. Each pressing section 80 brings the branch vessel 73 as close as possible to the base section 22 and removes the tissue surrounding the branch vessel 73, at the time when the branch vessel 73 is guided to the groove section 32 by the guide section 34.

The pressing section 80 is on the lower side (the first direction side) relative to the groove section 32. The pressing section 80 is provided on the base section 22 side in the side section 24, or on the side of a base of the side section 24, and protrudes toward the center in the width direction of the dissecting member 18. Due to this configuration, the pressing section 80 is close to the base section 22 (specifically, to the corner portion 23a of the base section 22). Specifically, the pressing section 80 shown as an example in FIG. 3 includes an arcuate-curved surface 82 constituting a lower side portion of the pressing section 80, and a tapered surface 84 constituting an upper side portion of the pressing section 80. The tapered surface 84 is inclined toward the groove section 32.

It is preferable that the shortest distance between the pressing section 80 and the base section 22 is substantially equal to or slightly greater than the outer diameter of the branch vessel 73. The shortest distance between the pressing section 80 and the base section 22 may also be smaller than the outside diameter of the branch vessel 73.

The first slit 86 is between the pressing section 80 and the base section 22 which permits the branch vessel 73 to pass therethrough. The second slit 88 is between the base section 22 and the side section 24. The second slit 88 communicates with the first slit 86 and is smoothly continuous with the groove section 32. The slit width of the first slit 86 is narrower than the slit width of the second slit 88. The first slit 86 may be curved. The second slit 88 is adjacent to the treatment region 33.

As shown in FIG. 2, the pressing section 80 extends parallel to the groove section 32. Specifically, the pressing section 80 extends in the axial direction of the first dissecting device 12, on the lower side (the first direction side) of the groove section 32. The length of the pressing section 80 along the axial direction of the first dissecting device 12 is greater than the length of the groove section 32. The distal end of the pressing section 80 is located distal to the distal end of the groove section 32. The proximal end of the pressing section 80 is located proximal to the proximal end of the groove section 32.

[Configuration of Second Dissecting Device 14]

As illustrated in FIG. 1, the second dissecting device 14 includes a grasping section 44 adapted (configured) to be graspable by the user, and a dissecting member 46 (second dissecting member) provided at a distal portion of the grasping section 44. As depicted in FIG. 5B, the grasping section 44 is a tubular member possessing an insertion lumen 45 in which an imaging device 17 can be inserted (i.e., is insertable). The grasping section 44 in the illustrated example possesses a rectilinear shape. Examples of the material constituting the grasping section 44 include rigid resins and metals. The insertion lumen 45 is a through-hole which extends along a longitudinal direction of the grasping section 44 and which opens at a distal surface and a proximal surface of the grasping section 44 (i.e., the proximal and distal ends of the insertion lumen 45 are open).

The dissecting member 46 includes a base part 48 fixed to a distal portion of the grasping section 44, a dissecting section 50 extending distally from a distal end of the base part 48, and two protruding sections 90 protruding in a thickness direction of the dissecting section 50 (in an upward direction in FIG. 5B) from both end portions in a width direction of the dissecting section 50.

"The thickness direction" in regard to the dissecting member 46 and the dissecting section 50 refers to a height direction (i.e., the Z-direction shown in FIG. 1) perpendicular to the axial direction (i.e., the X-direction shown in FIG. 1). The axial direction is the longitudinal direction of the second dissecting device 14 in FIG. 1. "The width direction" in regard to the dissecting member 46 and the dissecting section 50 refers to a direction (i.e., the Y-direction of FIG. 1) perpendicular to the axial direction (X-direction) and the height direction (Z-direction) of the dissecting member 46 in FIG. 1.

The base part 48 is formed in a hollow shape having a lumen 49 which extends along the longitudinal direction of the dissecting member 46. The distal end of the lumen 49 is closed by a distal end wall 48a of the base part 48. As indicated by an imaginary line in FIG. 5B, a front surface of the distal end wall 48a of the base part 48 is an inclined surface 48b inclined toward the upper side (the skin side) from the distal end toward the proximal end of the base part 48. The front surface of the distal end wall 48a of the base part 48 may be perpendicular to the axial direction of the second dissecting device 14.

The proximal end of the lumen 49 is an opening at a proximal surface of the base part 48. The diameter of a distal-side region of the lumen 49 is greater than the outside diameter of the grasping section 44. A distal portion of the grasping section 44 is inserted and fixed in a proximal-side region of the lumen 49 as illustrated in FIG. 5B. The lumen 49 includes a cavity 49a distal to the grasping section 44 into which a distal portion of the imaging device 17 can enter (i.e., the imaging device 17 is insertable into the cavity 49a).

The base part 48 in the illustrated example has a tetragon cross-sectional profile shape with rounded corners. The cross-sectional profile shape of the base part 48 may be another shape, such as a circle, an ellipse, and a trapezoid.

The dissecting member 46 (particularly, the base part 48) is transparent (light-transmitting). Examples of the dissecting member 46 material include glass and transparent resin. The base part 48 being transparent makes it is possible to image the front side and the surroundings of the base part 48 for observation by the imaging device 17 when the imaging device 17 is inserted in the insertion lumen 45. A reflecting section may be provided at a distal portion of the insertion lumen 45. The reflecting section may be oriented toward a blood vessel guide passage 54. The reflecting section may be integral with or separate from the insertion lumen 45. The reflecting section is formed, for example, of a transparent resin.

Although it is preferable that the dissecting member 46 is substantially colorless and transparent, the dissecting member 46 may be colored as long as it is transparent. The dissecting member 46 does not necessarily need to be entirely transparent. For example, only the base part 48 (particularly, only the distal end wall 48a functioning as an observation window) may be transparent. The distal end wall 48a of the dissecting member 46 does not necessarily need to be formed integrally with the other portion. The distal end opening of the cavity 49a may thus be closed with a separate transparent member.

Figure 5A:
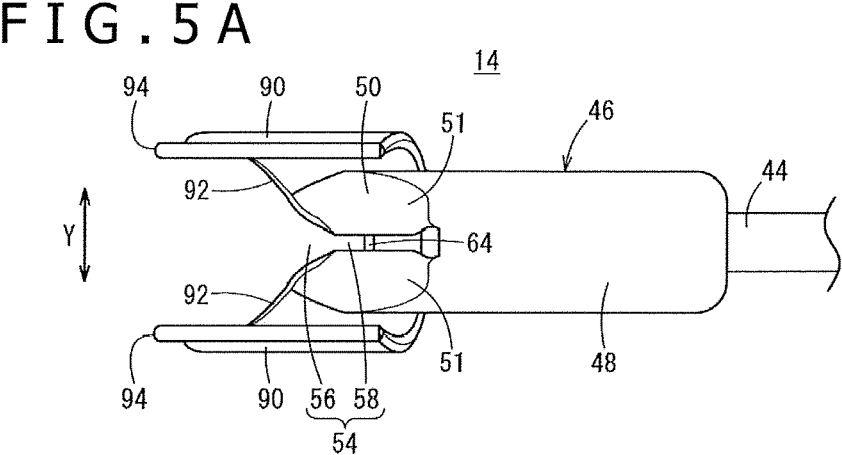
FIG. 5A is a plan view of a distal portion of a second dissecting device.
Figure 5B:
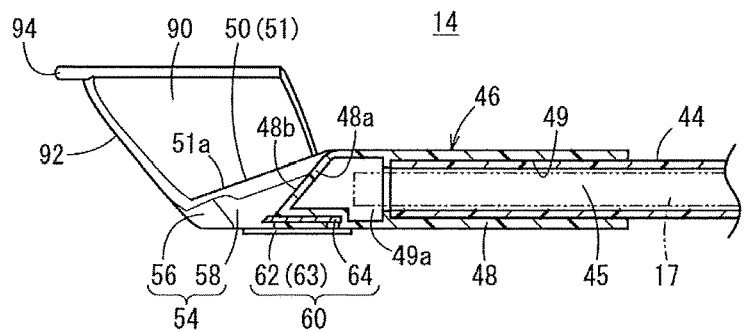
FIG. 5B is a sectional view of the distal portion of the second dissecting device.

As shown in FIGS. 1 and 5A, the dissecting section 50 includes a pair of dissecting portions 51 which dissect tissue (fat 74 or the like) when the dissecting member 46 is moved forward along a blood vessel 72. The pair of dissecting portions 51 are spaced apart from one another in the width direction of the dissecting member 46 (the Y-direction).

The thickness (the dimension measured in the height direction of the dissecting member 46) of each dissecting portion 51 gradually increases in the proximal direction as shown in FIG. 5B, so that tissue is easily dissected by the dissecting member 46 in the direction of alignment of the blood vessel 72. Specifically, each dissecting portion 51 has an inclined surface 51a inclined toward the upper side (the skin side) from the distal end to the proximal end of the inclined surface 51a. The distal end of the dissecting portion 51 is located distal to the distal end of the base part 48.

The distal portion of the dissecting member 46 includes the blood vessel guide passage 54 by which a branch vessel 73 is accepted and guided toward the base part 48 side. The blood vessel guide passage 54 is formed between the pair of dissecting portions 51. The blood vessel guide passage 54 penetrates the dissecting member 46 in the thickness direction of the dissecting member 46. The blood vessel guide passage 54 is an opening in the distal direction of the dissecting member 46, to the upper side of the dissecting member 46, and to the lower side of the dissecting member 46. A front surface of the distal end wall 48a of the base part 48 faces a proximal portion of the blood vessel guide passage 54. The height of the blood vessel guide passage 54 perpendicular to the longitudinal direction of the second dissecting device 14 increases in proportion to the increase, in the proximal direction, of the thickness of the dissecting section 50 in the height direction perpendicular to the longitudinal direction of the second dissecting device 14.

The blood vessel guide passage 54 includes a first groove section 56 (introducing section) constituting a distal-side region of the blood vessel guide passage 54, and a second groove section 58 constituting a proximal-side region of the blood vessel guide passage 54. As illustrated in FIG. 5A, the first groove section 56 has a width that decreases in the proximal direction (i.e., the width of the first groove section 56 decreases from the distal end to the proximal end of the first groove section 56). The width of the first groove section 56 is greater than the width of the second groove section 58. The second groove section 58 is a rectilinear groove which communicates with the first groove section 56 and which extends along the longitudinal direction of the dissecting member 46.

Figure 5C:
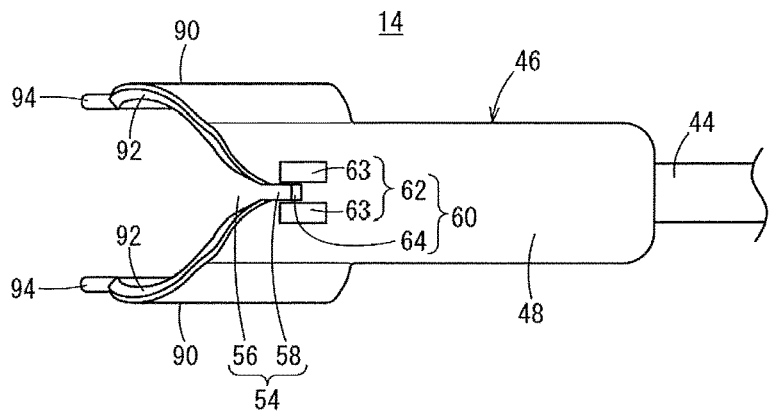
FIG. 5C is a bottom view of the distal portion of the second dissecting device.

As shown in FIGS. 5B and 5C, the dissecting member 46 includes a treating section 60 (second treating section) for stanching and cutting the branch vessel 73. The treating section 60 includes a stanching section 62 for stanching the branch vessel 73, and a cutting section 64 (a cutting edge) for cutting the branch vessel 73. The stanching section 62 has a bipolar structure including a pair of electrodes 63. The pair of electrodes 63 are provided respectively on both sides in the width direction of the second groove section 58. In the example embodiment illustrated in FIGS. 5A-5C, the pair of electrodes 63 are attached to the bottom surface of the dissecting member 46. The pair of electrodes 63 may also be embedded in the dissecting member 46.

Application of a high-frequency voltage between the pair of electrodes 63 permits the branch vessel 73 guided into the second groove section 58 to be stanched by cauterization (thermal coagulation). The cutting section 64 is provided at a deepest part (proximal part) of the second groove section 58 and is proximal to the distal end of each electrode of the pair of electrodes 63. This relative positioning helps ensure that the cauterized branch vessel 73 can be cut by the cutting section 64. When the cutting section 64 is additionally an electrode, application of a high-frequency voltage between the cutting section 64 and the electrode 63 permits the branch vessel 73 guided into the second groove section 58 to be stanched by cauterization (thermal coagulation). These high-frequency voltages may be applied simultaneously or may be applied in a switching manner by use of a switch.

The width of the second groove section 58 may be constant along the lengthwise direction of the second groove section 58, or the second groove section 58 width may gradually decrease in the proximal direction (i.e., from the distal end to the proximal end of the. The width of the second groove section 58 is preferably smaller than the outside diameter of the branch vessel 73. This makes it possible to press the branch vessel 73 flat within the second groove section 58, and therefore to reliably perform the cauterization at the stanching section 62.

The protruding sections 90 are formed in a plate-like shape (i.e., plate-shaped). As depicted in FIG. 5A, the protruding sections 90 are spaced apart in the width direction of the dissecting section 50 (the Y-direction), and extend in the axial direction of the second dissecting device 14 (as shown in the plan view of FIG. 5A). Distal ends of the protruding sections 90 are located distally of distal ends of the dissecting section 50. In addition, the distal ends of the protruding sections 90 are located on outer sides in the width direction of the dissecting device 50 as compared to both end portions in the width direction of the dissecting section 50 (i.e., the distal ends of the protruding sections 90 are outside of the end portions of the dissecting section 50 in the width direction).

Figure 6:
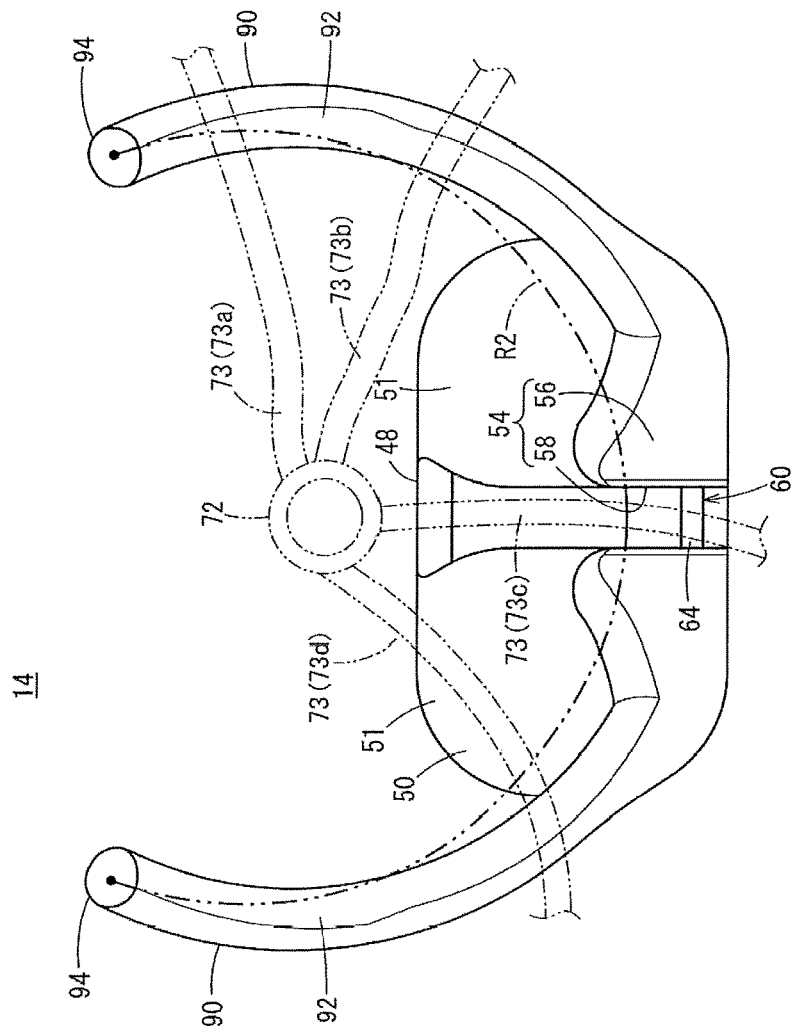
FIG. 6 is a front view of the second dissecting device.

As illustrated in FIG. 6, each protruding section 90 is curved, on a base side of the protruding section 90, to be displaced toward the inside with respect to the width direction of the dissecting section 50. Each protruding section 90 is curved to bulge toward the outside in the width direction of the dissecting section 50 (i.e., each protruding section 90 is convex and curves to bulge/protrude outward in the Y-direction). In other words, the distance between the two protruding sections 90 is greater at intermediate portions in the protruding direction of the protruding sections 90 than the distance between the two protruding sections 90 at the protruding ends and bases of the two protruding sections 90.

As illustrated in FIG. 6, the protruding ends (upper ends) of the protruding sections 90 are located above the base part 48 and the dissecting section 50. The thickness (plate thickness) of the protruding section 90 is substantially constant from the base to the protruding end of the protruding section 90. In another embodiment, the thickness of the protruding section 90 may decrease toward the protruding end side of the protruding section 90. In other words, the thickness of the protruding section 90 on the protruding end side may be smaller than the thickness of the protruding section 90 on the base side.

The length of the protruding section 90 shown in FIG. 5B along the axial direction of the second dissecting device 14 is substantially constant from the base to the protruding end of the protruding section 90. In another embodiment, the length of the protruding section 90 along the axial direction of the second dissecting device 14 may increase toward the protruding end side of the protruding section 90. In other words, the length of the protruding section 90 along the axial direction of the second dissecting device 14 may be greater on the protruding end side than on the base side.

As depicted in FIG. 5B, each protruding section 90 has a guide section 92 (second guide section) that guides the branch vessel 73 toward the treating section 60. The guide section 92 is an edge portion of the protruding section 90 on the distal side of the protruding portion 90. The guide section 92 is inclined such as to be displaced upward in going distally (i.e., the guide section 92 gradually inclines upward from the proximal end to the distal end of the guide section 92). Therefore, a portion of the guide section 92 on the side of the protruding end of the protruding section 90 is located distal to a portion of the guide section 92 on the side of the base of the protruding section 90.

A distal projection 94 which projects distally is at a distal portion of each protruding section 90. The dissecting member 46 captures the branch vessel 73 coming into contact with the distal projection 94 or a part on the lower side of the distal projection 94 when the dissecting member 46 is moved forward within a living body along a blood vessel 72 on the lower side (the fascia 76 side) of the blood vessel 72. The dissecting member 46 guides the branch vessel 73 toward the dissecting section 50 side. Specifically, the guide section 92 shifts (i.e., applies a force to urge) the branch vessel 73 contacting the guide section 92 toward the lower side, and guides the branch vessel 73 toward the dissecting section 50. A capture range R2 is indicated by an imaginary line in FIG. 6. The dissecting member 46 having the guide sections 92 configured in this manner can capture the branch vessels within this capture range R2.

Branch vessels 73a to 73d illustrated in FIG. 6 fall within the capture range R2, and, therefore, the branch vessels 73a to 73d are guided by the guide sections 92 toward the dissecting section 50 when the dissecting member 46 is moved forward along the blood vessel 72 on the lower side of the blood vessel 72. The branch vessels 73a to 73d are then guided by the blood vessel guide passage 53 of the dissecting section 50 to the treating section 60. FIG. 6 specifically illustrates the branch vessel 73c being guided by the blood vessel guide passage 54 to the treating section 60. On the other hand, when there are blood vessels 73 that fall out of the capture range R2, such blood vessels 73 are not captured by the dissecting member 46.

A positional relation between the capture range R1 within which capture of the branch vessels 73 by the dissecting member 18 of the first dissecting device 12 is possible and the capture range R2 within which capture of the branch vessels 73 by the dissecting member 46 of the second dissecting device 14 is possible will be described in reference to FIG. 7. The guide sections 34 and the guide sections 92 are formed such that, when tissue is dissected by the first dissecting device 12 with the base section 22 disposed on one side (the upper side) in a radial direction of the blood vessel 72 and the tissue is dissected by the second dissecting device 14 with the dissecting section 50 disposed on the other side (the lower side) in the radial direction of the blood vessel 72, the capture range R1 (within which capture of the branch vessels 73 by the dissecting member 18 is possible) and the capture range R2 (within which capture of the branch vessels 73 by the dissecting member 46 is possible) overlap with each other in the radial direction of the blood vessel 72.

Figure 7:
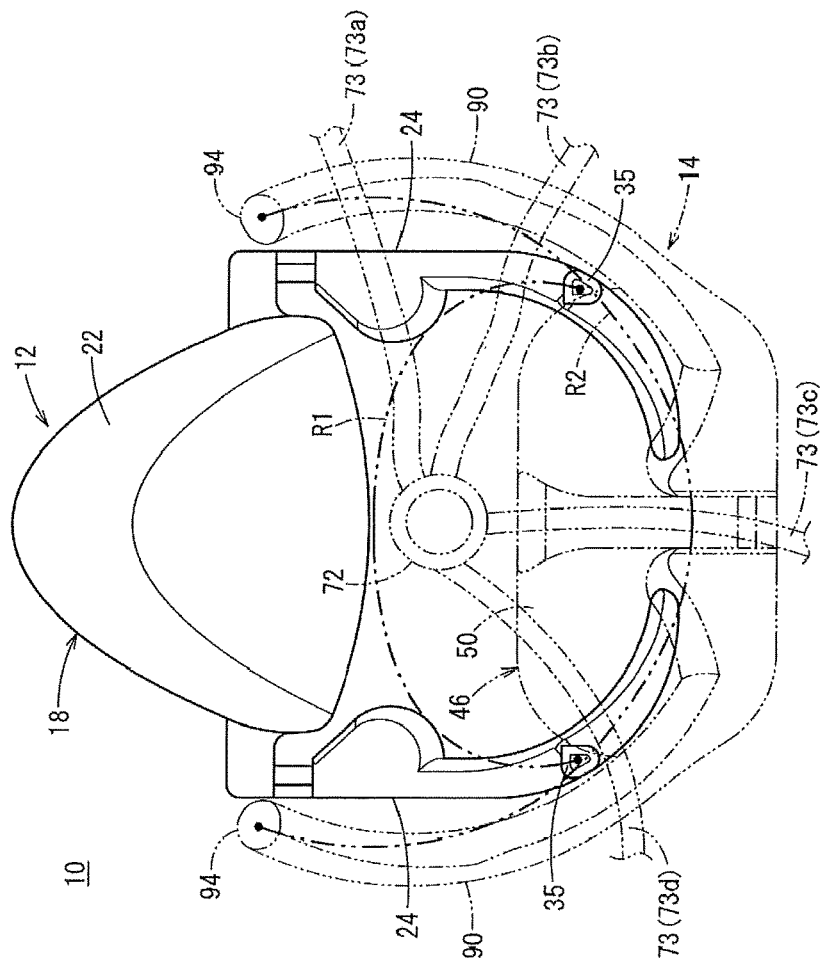
FIG. 7 illustrates a positional relation between a capture range within which a first dissecting member of the first dissecting device can capture the branch vessels and a capture range within which a second dissecting member of the second dissecting device can capture the branch vessels.

In other words, the capture range R1 and the capture range R2 overlap with each other in the vertical direction as illustrated in FIG. 7. Specifically, positions where the distal projections 94 of the dissecting member 46 pass when the dissecting member 46 is moved forward within the living body along the blood vessel 72 are located above positions where the distal projections 35 of the dissecting member 18 pass when the dissecting member 18 is moved forward within the living body along the blood vessel 72. With the capture range R1 and the capture range R2 configured in the above-described manner, the branch vessels 73 can be captured in all directions around the blood vessel 72.

Additionally, when tissue is dissected by one of the first dissecting device 12 and the second dissecting device 14 and then the tissue is dissected by the other of the first dissecting device 12 and the second dissecting device 14, the other device passes outside of the tissue part where the one device passed. This is illustrated in FIG. 7, wherein the second dissecting device 14 passes outside of the part where the first dissecting device 12 has passed. More specifically, the positions where the distal projections 94 of the dissecting member 46 pass when the dissecting member 46 is moved forward within the living body along the blood vessel 72 are located outside of the positions where the distal projections 35 of the dissecting member 18 pass when the dissecting member 18 is moved forward within the living body along the blood vessel 72.

[Blood Vessel Harvesting Method]

A blood vessel harvesting method in which the dissecting system 10 is used is described below. The blood vessel harvesting method includes a dissecting step (first step) of dissecting a blood vessel 72 by using the dissecting system 10 when the blood vessel 72 is covered with surrounding fat 74 (tissue), a cutting step (second step) of cutting after ligating the blood vessel 72, and an extracting step (third step) of extracting the blood vessel 72 while the blood vessel is covered with the surrounding fat 74 from the living body. In this example, a case of harvesting a saphenous vein in a lower limb will be explained.

Figure 8:
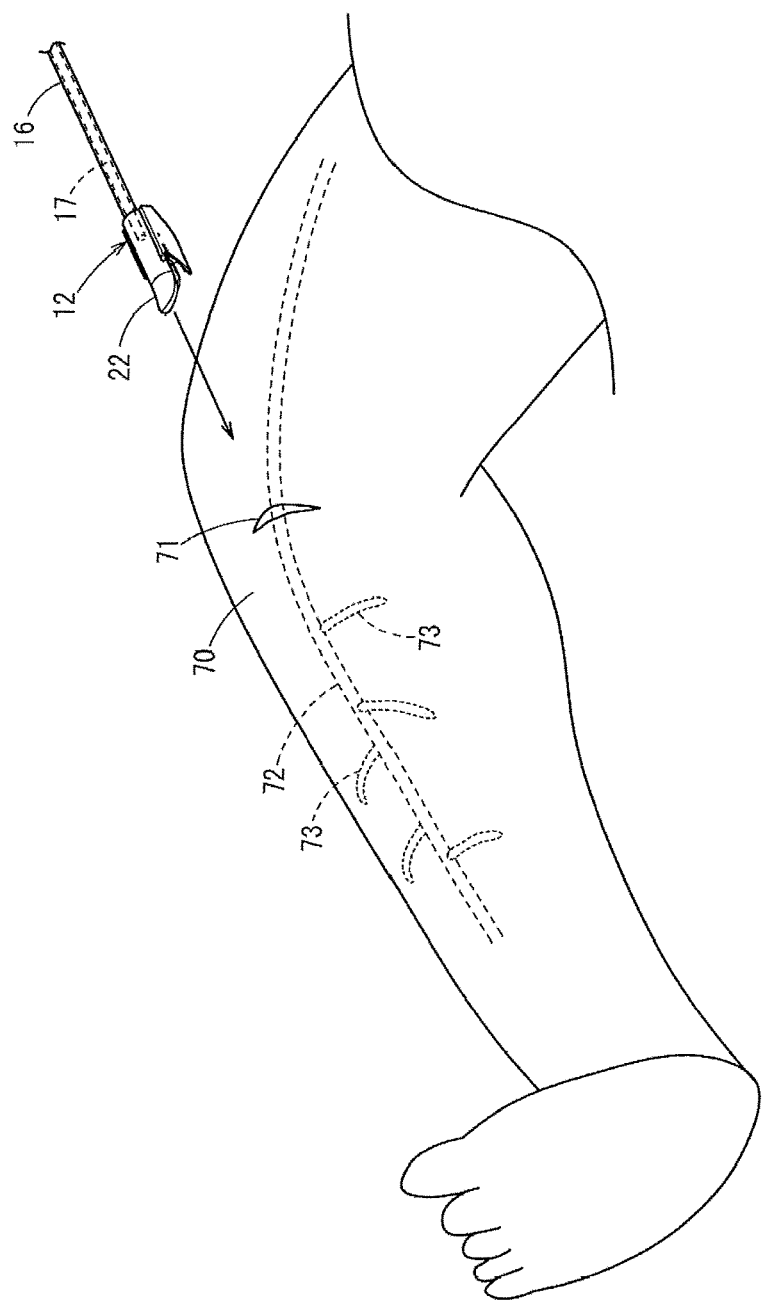
FIG. 8 illustrates a method of inserting the first dissecting device into a living body.

In the dissecting step, first, the position of the blood vessel 72 to be harvested is confirmed. The patient's skin 70 is incised to create an incision 71 based on the position, as illustrated in FIG. 8, for example. After the skin 70 is incised, the fat 74 is dissected (e.g., separated) until the blood vessel 72 appears (until the blood vessel 72 or a saphenous fascia is exposed). Next, the first dissecting device 12 is prepared with the imaging device 17 inserted in the first dissecting device 12. The first dissecting device 12 may be preliminarily provided with the imaging device 17 as a component of the first dissecting device 12.

The first dissecting device 12 is then inserted into the living body along the blood vessel 72 via the incision 71 while an operator observes the inside of the living body through the imaging device 17. The first dissecting device 12 is inserted in such a manner that the base section 22 of the dissecting member 18 is disposed between the skin 70 and the blood vessel 72, and the first dissecting device 12 is inserted so that the thickness direction of the base section 22 coincides with the direction of alignment of the base section 22 with the blood vessel 72.

Figure 9:
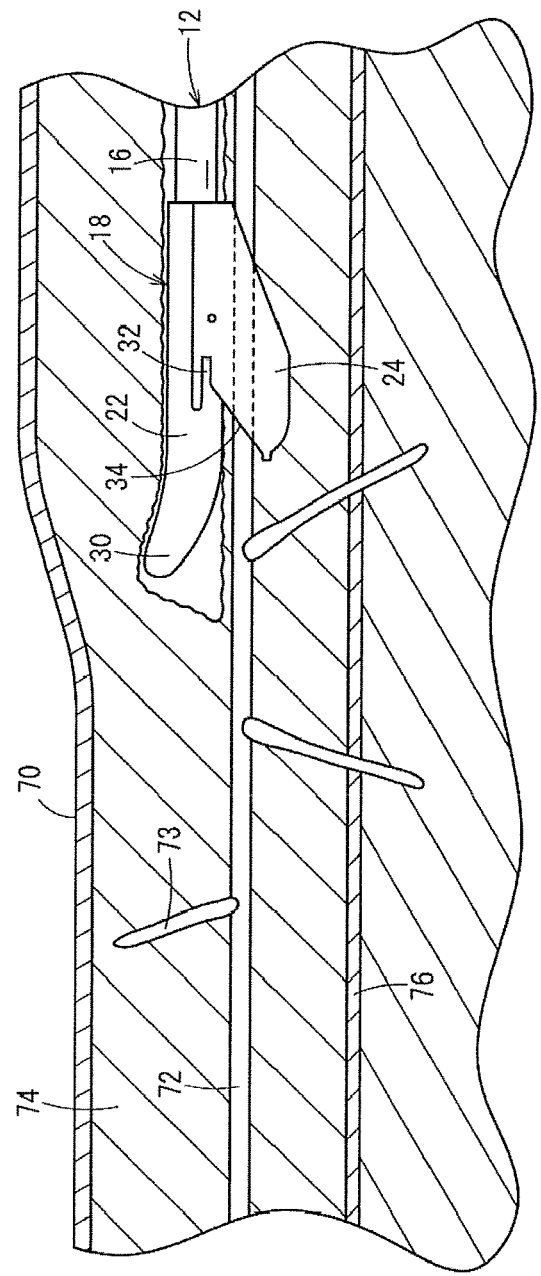
FIG. 9 is a sectional view along an extending direction of a blood vessel in a living body, which illustrates the first dissecting device being pushed forward in the living body along the blood vessel.

The first dissecting device 12 is then moved forward along the blood vessel 72 in the living body by a distance corresponding to a required length (a length to be harvested). As illustrated in FIG. 9, the first dissecting device 12 moves forward while dissecting the fat 74 surrounding the blood vessel 72 by the dissecting member 18. Specifically, the distal dissecting section 30 of the base section 22 dissects the fat 74 present on the upper side (the skin 70 side) of the blood vessel 72 in the thickness direction of the base section 22.

Figure 10:
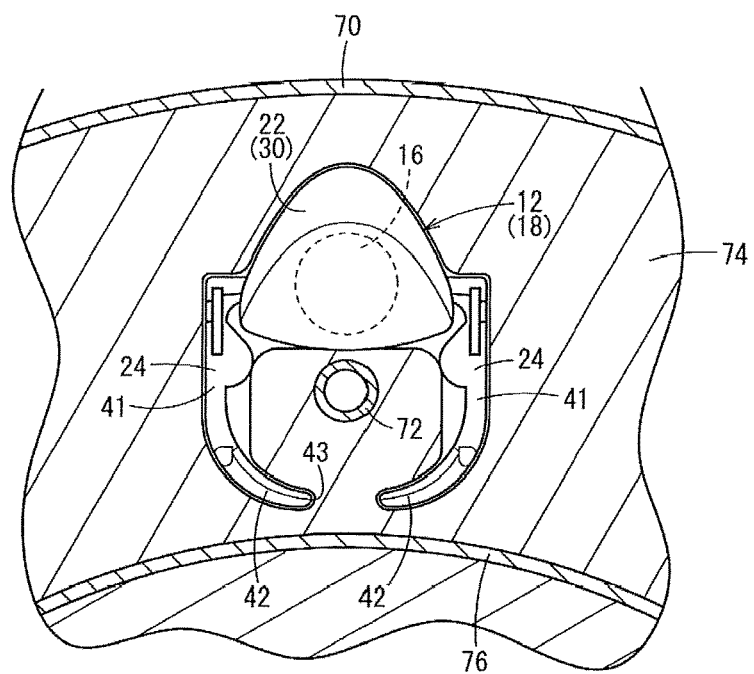
FIG. 10 is a sectional view along a direction perpendicular to a blood vessel in a living body, which illustrates the first dissecting device being pushed forward in the living body along the blood vessel.

As shown in FIG. 10, the pair of side sections 24 dissect the fat 74 on the lateral sides of the blood vessel 72 (i.e., in the Y-direction) and the lower side (the fascia 76 side) of the blood vessel 72 in the thickness direction of the side sections 24 (in the Z-direction). Specifically, the side wall portions 41 dissect the fat 74 on the lateral sides of the blood vessel 72 in the thickness direction of the side wall portions 41 (in the width direction of the base section 22 or in the Y-direction). In addition, the projecting portions 42 dissect the fat 74 present on the lower side (the fascia 76 side) of the blood vessel 72 (exclusive of a part in the space 43) in the thickness direction of the projecting portions 42.

Figure 11A:
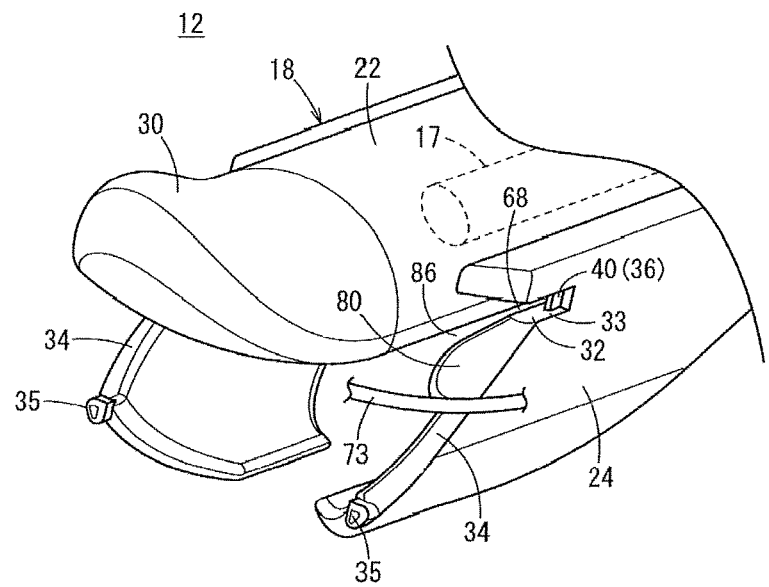
FIG. 11A is a first view for explaining capture of a branch vessel by the first dissecting device.

When the first dissecting device 12 is moved forward within the living body along the blood vessel 72, as shown in FIG. 11A, the branch vessel 73 present in the capture range R1 (see FIG. 3) is guided by the guide section 34 into the groove section 32. The branch vessel 73 is smoothly guided toward the groove section 32 side by the guide section 34 which is inclined.

Figure 11B:
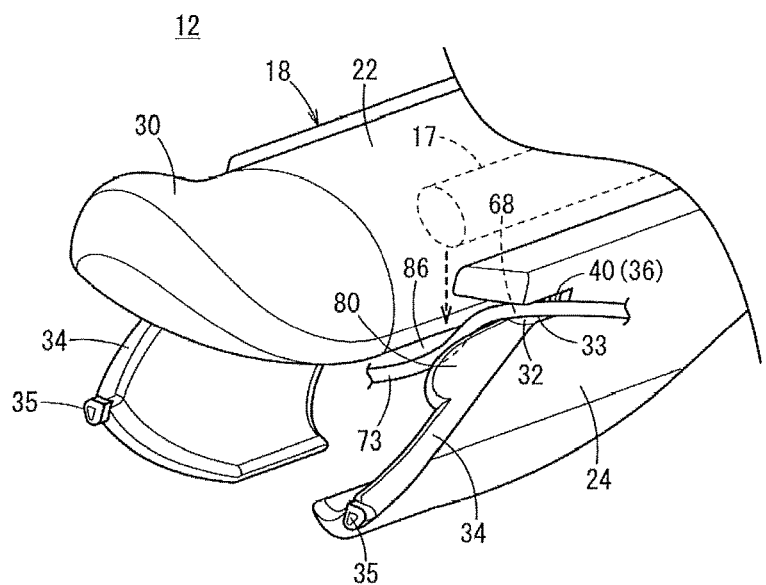
FIG. 11B is a second view for explaining the capture of the branch vessel by the first dissecting device.

Then, when the first dissecting device 12 is moved further forward within the living body, the branch vessel 73 reaches the treatment region 33 of the groove section 32 as depicted in FIG. 11B. The branch vessel 73 is next stanched and cut by the treating section 36 (see FIG. 2). A branch vessel 73 that comes into contact with the lower side of the distal projections 35 of the side sections 24 at the time of contact of the dissecting member 18 with the branch vessel 73 is guided into the space 43 between the pair of projecting portions 42 and, therefore, is not subjected to stanching and cutting by the treating section 36.

The branch vessel 73 is introduced into the groove section 32 of the first dissecting device 12 while the pressing section 80 is pressing the branch vessel 73 toward the base section 22 side. This configuration makes it possible to reduce the distance between the imaging device 17 inserted in the cavity 28 of the base section 22 and the branch vessel 73 and to remove the tissue (fat 74) surrounding the branch vessel 73. Therefore, the user can easily observe (visually confirm) the branch vessel 73 by the imaging device 17 and can efficiently perform the treatment of the branch vessel 73.

Since the pressing section 80 is on the base section 22 side in the side section 24, the distance between the base section 22 and the pressing section 80 is reduced. The visibility of the branch vessel 73 by the imaging device 17 can thus be effectively further enhanced. The branch vessel 73 can also be effectively pressed toward the base section 22 side because the pressing section 80 protrudes toward the center in the width direction of the dissecting member 18 (i.e., Y-direction).

The branch vessel 73 can be pressed toward the base section 22 side in the vicinity of the groove section 32 by the pressing section 80 while the branch vessel 73 is moved within the groove section 32 because the pressing section 80 extends in parallel to the groove section 32. Therefore, the visibility of the branch vessel 73 can be enhanced even while the branch vessel 73 is moved within the groove section 32.

The first slit 86 of the first dissecting device 12 as illustrated in FIG. 3 permits the branch vessel 73 to pass through the first slit 86 and is formed between each pressing section 80 and the base section 22. Therefore, the distance between the base section 22 and the pressing section 80 can be reduced effectively. The second slit 88 that communicates with the first slit 86 and is smoothly continuous with the groove section 32 is formed between the base section 22 and the side section 24. Therefore, the branch vessel 73 can be smoothly guided from the first slit 86 to the groove section 32. For example, the first slit 86 may be rectilinear in shape, and the second slit 88 may be curved. In another embodiment, the first slit 86 may be curved, and the second slit 88 may be rectilinear in shape. Both of the first slit 86 and the second slit 88 may be rectilinear or curved in shape.

The treatment region 33 is disposed in such a manner that the space 68 (into which tissue is inhibited from entering) is formed between the treatment region 33 and the base section 22. This helps ensure that when the tissue (fat 74 or the like) surrounding the blood vessel 72 is dissected by the dissecting member 18 in the living body, the tissue is inhibited from entering into the space 68 between the base section 22 and the treatment region 33. A branch vessel 73 that has entered into the space 68 can thus be observed (visually confirmed) via the imaging device 17 inserted in the cavity 28 of the base section 22, without the field of view being obstructed by the tissue. Therefore, the treatment of the branch vessel 73 can be efficiently carried out while a user or operator observes the treatment through the imaging device 17.

The dissecting member 18 has wall portions defining the spaces 68. The position at which the dissection interfaces Sa of tissue are formed can be determined by the wall portions, so that the spaces 68 into which tissue is inhibited from entering can be easily secured. The wall portions are also parts of the bottom portion 23 of the base section 22, and the treatment regions 33 are located on the upper side (the second direction side) of the bottom portion 23. The spaces 68 into which tissue is prevented from entering can be easily constructed with the positions of the treatment regions 33 configured in this manner.

The treatment regions 33 are provided above the corner portions 23a of the bottom portion 23 and are therefore located above the dissection interfaces Sa, so that tissue can be reliably prevented from entering into the spaces 68. Since the treatment regions 33 are provided on the base side of the side sections 24, entering of tissue into the spaces 68 can be prevented effectively.

After the first dissecting device 12 is moved forward by a distance corresponding to a required length (e.g., a predetermined distance), the first dissecting device 12 is withdrawn out of the living body via the incision 71 shown in FIG. 8.

Figure 16:
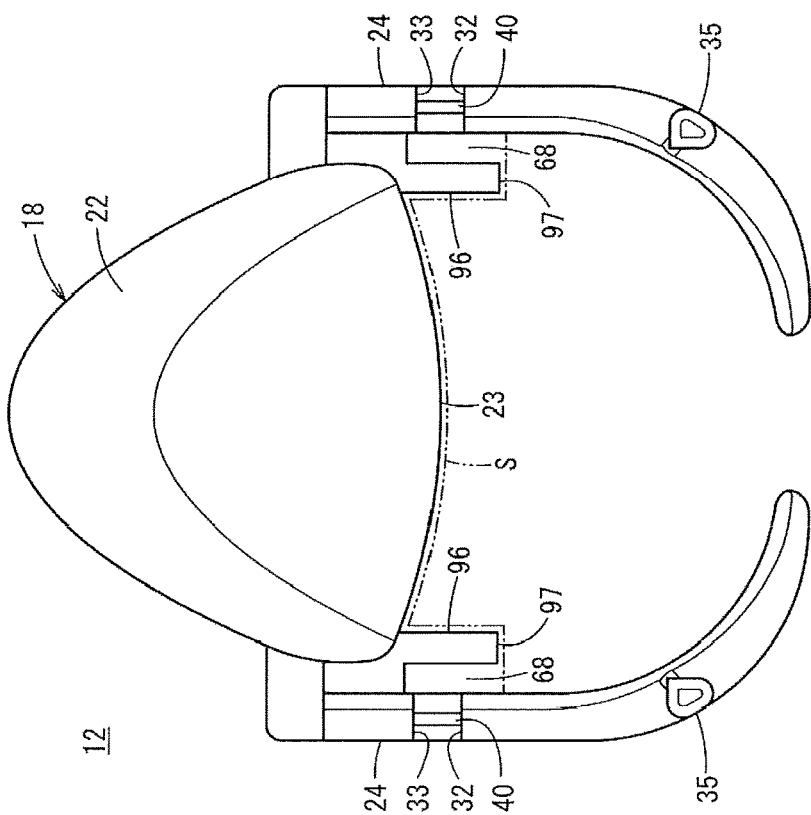
FIG. 16 is a front view of a first dissecting device provided with a treatment region below a bottom portion of a base section.

As illustrated in FIG. 16, the treatment regions 33 of the dissecting member 18 may be disposed on the lower side (the first direction side) relative to the bottom portion 23 of the base section 22. In this embodiment, the dissecting member 18 includes wall portions 96 which define the spaces 68. The wall portions 96 protrude below the bottom portion 23 of the base section 22, and face the groove section 32 and the treatment region 33. Protruding end surfaces 97 (lower surfaces) of the wall portions 96 are located below the treatment regions 33. The wall portions 96 protrude from the bottom portion 23. The wall portion 96 may not only protrude downward from the bottom portion 23 but also could protrude downward from an inner side surface (a side surface on the base section 22 side) of the side section 24.

At a part where the wall portion 96 is provided, a dissection interface of tissue (fat 74) is formed in the vicinity of the treatment region 33 by the protruding end surface 97 of the wall portion 96. The tissue does not enter above the protruding end surface 97 of the wall portion 96 in the vicinity of the treatment region 33. Therefore, even when the treatment regions 33 are below the bottom portion 23 of the base section 22, the spaces 68 into which tissue does not enter can be formed by the wall portions 96 which protrude downward.

After the first dissecting device 12 is withdrawn out of the living body, an insertion step is conducted of inserting the second dissecting device 14 (with the imaging device 17 inserted in the second dissecting device 14) into the incision 71. The dissecting member 46 is in an inverted state (with the protruding side of the protruding sections 90 of the dissecting member 46 oriented toward the interior of the living body) as illustrated in FIG. 12 when the second dissecting device 14 is inserted into the living body. The second dissecting device 14 may instead preliminarily be provided with the imaging device 17 as a component of the second dissecting device 14.

Figure 13A:
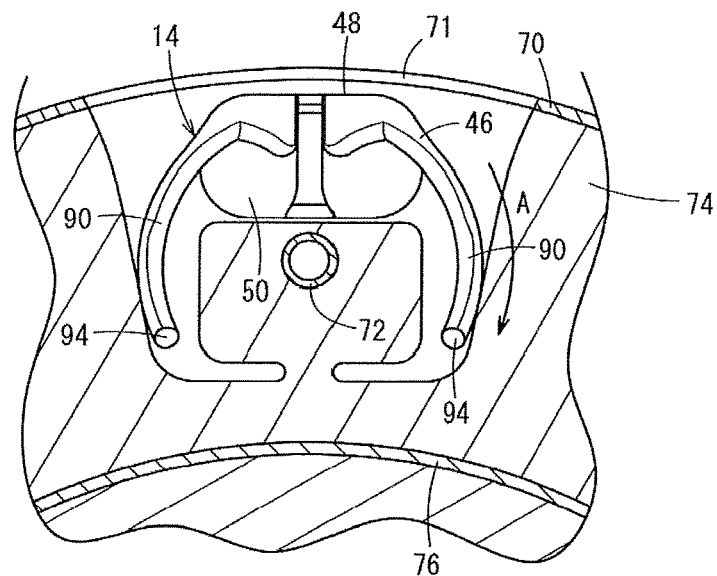
FIG. 13A is a first view for explaining a method of placing a dissecting member of the second dissecting device in a living body.

The two protruding sections 90 are inserted into the fat 74 via the incision 71 provided in the skin 70 in the insertion step depicted in FIG. 13A. The two protruding sections 90 are inserted so that the blood vessel 72 is disposed between the two protruding sections 90. This positioning helps ensure that the dissecting member 46 is inserted into the fat 74 with the two protruding sections 90 avoiding the blood vessel 72.

Figure 13B:
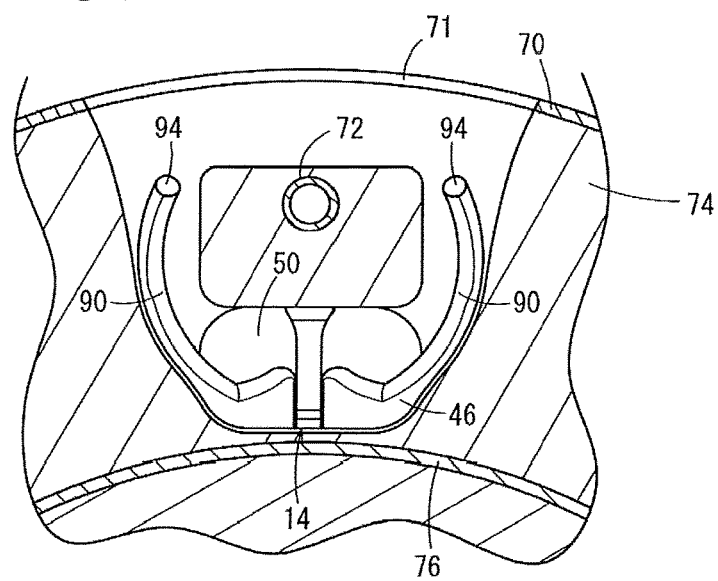
FIG. 13B is a second view for explaining the method of placing the dissecting member of the second dissecting device in the living body.

After the insertion step, a rotation step is performed in which the dissecting member 46 is rotated (e.g., reversed in orientation) around the blood vessel 72. Specifically, as indicated by arrow A in FIG. 13A, the dissecting member 46 is rotated half a turn (180°) around the blood vessel 72. As a result of the rotation, the dissecting member 46 is disposed in the fat 74 on the lower side of the blood vessel 72 (in the fat 74 between the blood vessel 72 and the fascia 76), as depicted in FIG. 13B. The protruding sections 90 protrude upward (toward the skin 70 side) after the rotation as illustrated in FIG. 13B.

When the dissecting member 46 is rotated, the protruding sections 90 dissect the fat 74 that has not been dissected by the first dissecting device 12 under the blood vessel 72 in the vertical direction (in the direction of alignment of the blood vessel 72 with the fascia 76). The base part 48 and the dissecting section 50 lift the blood vessel 72 upward (toward the skin 70 side). Insertion resistance at the time of inserting the protruding sections 90 into the fat 74 for disposing the dissecting member 46 in the living body is reduced when the thickness of the protruding sections 90 decreases toward the protruding end side of the protruding sections 90. The insertion resistance is also reduced when the axial length of the protruding sections 90 decreases toward the protruding end side of the protruding sections 90.

Figure 14A:
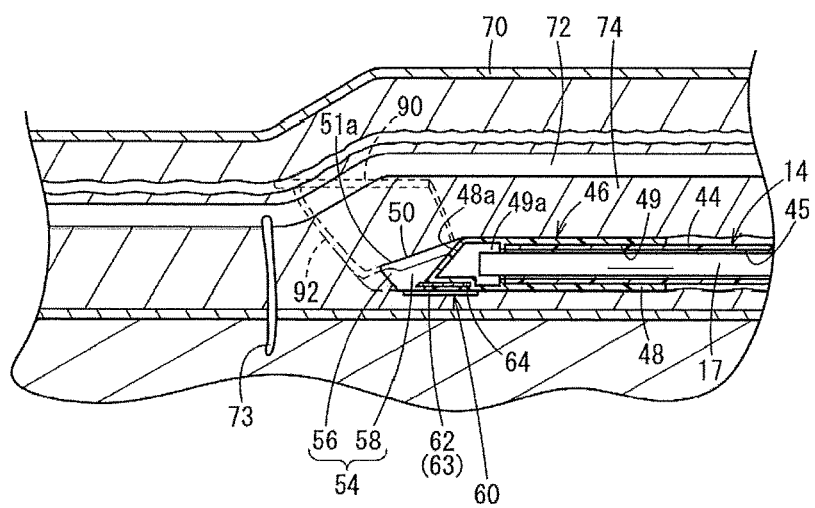
FIG. 14A is a sectional view along an extending direction of a blood vessel in a living body, which illustrates the second dissecting device being pushed forward in the living body along the blood vessel.

The second dissecting device 14 is then moved forward along the blood vessel 72 within the fat 74 in the living body by a distance corresponding to the required length (e.g., the predetermined length to be harvested). The second dissecting device 14 is moved forward in the fat 74 on the lower side of the blood vessel 72 and dissects the fat 74 by the dissecting section 50 of the dissecting member 46 while forcing open the fat 74 and lifting the blood vessel 72 to the upper side (the skin 70 side) along the inclined surface 51a of the dissecting section 50 as depicted in FIG. 14A. Specifically, the dissecting section 50 lifts the blood vessel 72 towards the upper side (the skin 70 side) while the fat 74 on the lower side of the blood vessel 72 is being dissected by the dissecting section 50 from the fat 74 on the lower side of the second dissecting device 14 in the thickness direction of the dissecting member 46 (in the direction of alignment of the dissecting member 46 with the blood vessel 72). As a result, a dissected part is formed in such a manner as to surround the whole perimeter of the blood vessel 72. In other words, the fat 74 is dissected over the whole circumferential range of the perimeter of the blood vessel 72.

Figure 14B:
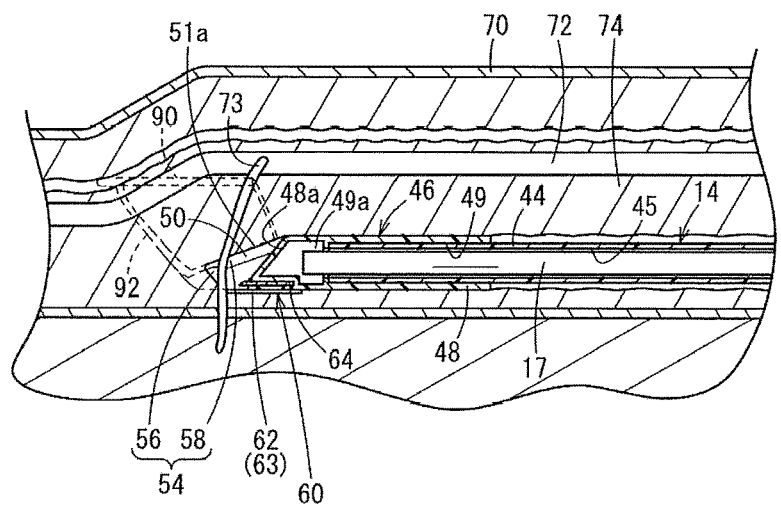
FIG. 14B is a sectional view showing a state in which the second dissecting device has been further pushed forward.

When the second dissecting device 14 is moved forward within the living body along the blood vessel 72, as shown in FIG. 14B, the second dissecting device 14 moves forward in the fat 74 on the lower side of the blood vessel 72 and dissects the fat 74 by the dissecting section 50 of the dissecting member 46 while forcing open the fat 74 and lifting the blood vessel 72 toward the upper side (the skin 70 side) along the inclined surface 51a of the dissecting section 50. Specifically, the dissecting section 50 lifts the blood vessel 72 towards the upper side (the skin 70 side) while the fat 74 on the lower side of the blood vessel 72 is being dissected by the dissecting section 50 from the fat 74 on the lower side of the second dissecting device 14 in the thickness direction of the dissecting member 46 (in the direction of alignment of the dissecting member 46 with the blood vessel 72). The branch vessel 73 is thus stretched and is exposed from the fat 74. The exposed branch vessel 73 can then be guided by the blood vessel guide passage 54 to the distal end wall 48a of the base part 48 and the treating section 60. Next, the branch vessel 73 is brought into contact with the distal end wall 48a of the base part 48. The branch vessel 73 is then stanched and cut by the treating section 60.

When the second dissecting device 14 is moved forward within the living body along the blood vessel 72, the second dissecting device 14 guides the branch vessels 73 present within the capture range R2 (see FIG. 6) to the treating section 60 by the guide sections 92 and the blood vessel guide passage 54, or by the blood vessel guide passage 54. The branch vessels 73 are thus smoothly guided toward the treating section 60 by the inclined guide sections 92 or the first groove section 56.

The capture range R1 within which capture of the branch vessels 73 by the dissecting member 18 of the first dissecting device 12 is possible and the capture range R2 within which capture of the branch vessels 73 by the dissecting member 46 of the second dissecting device 14 is possible overlap each other in the radial direction of the blood vessel 72 as illustrated in FIG. 7. When the first dissecting device 12 is used first (i.e., inserted into the body before the second dissecting device 12), the branch vessels 73c and 73d falling out of the capture range R1 are not captured. These branch vessels 73c and 73d, however, fall within the capture range R2 of the second dissecting device 14 which is inserted after the first dissecting device 12, and so the user can reliably capture the branch vessels 73c and 73d that could not be successfully captured by the first-used device by using the second dissecting device 14 after the first dissecting device 12.

When tissue is dissected by one of the first dissecting device 12 and the second dissecting device 14 (in the illustrated example, the first dissecting device 12) and thereafter the tissue is dissected by the other of the first dissecting device 12 and the second dissecting device 14 (in the illustrated example, the second dissecting device 14), the other device (i.e., the second of the two dissecting devices 12 and 14 inserted into the living body) passes outside of the part where the one device has passed. In other words, the two dissecting devices 12 and 14 are configured to move along different (i.e., non-overlapping) paths within the living body near an outside of the blood vessel 72. Therefore, the tissue on the side of harvesting that has been dissected by the first-used device can be restrained from being damaged by the secondly-used device. If the second dissecting device 14 is used first (i.e., inserted into the living body first) and thereafter the first dissecting device 12 is used, a configuration is preferably adopted wherein the first dissecting device 12 passes outside of the part where the second dissecting device 14 has passed.

The first groove section 56 of the blood vessel guide passage 54 guides the branch vessel 73 (which has been urged toward the first groove section 56 by the guide sections 92) toward the second groove section 58. The second groove section 58 guides the branch vessel 73 to the distal end wall 48a of the base part 48 and the treating section 60. Then, the branch vessel 73 is brought into contact with the distal end wall 48a of the base part 48, and the branch vessel 73 guided to the treating section 60 is stanched (cauterized) by the stanching section 62 and thereafter cut by the cutting section 64. The branch vessel 73 may be guided to the treating section 60 without being put into contact with the distal end wall 48a of the base part 48.

After the second dissecting device 14 is moved forward by a distance corresponding to the required length (i.e., a predetermined distance), the second dissecting device 14 is withdrawn out of the living body via the incision 71.

Dissecting the blood vessel 72 when the blood vessel 72 is covered with the fat 74 (tissue) is completed by the above-described operations.

As has been described above, the branch vessel 73 can be drawn near and guided to the treating section 60 by the guide sections 92 provided in the protruding sections 90 protruding from the dissecting section 50 of the second dissecting device 14 when the dissecting member 46 moves forward within the living body. The capture range for the branch vessels 73 can be widened because the second dissecting device 14 includes the guide sections 92. This enables the branch vessels 73 that cannot be successfully captured by the dissecting section 50 alone to be captured and efficiently treated by the treating section 60. The captured branch vessel 73 can also be easily treated while an operator observes the branch vessel 73 via the imaging device 17 inserted in the insertion lumen 45 of the grasping section 46.

The capture range for the branch vessels 73 can be further widened by spacing apart the two protruding sections 90 in the width direction of the dissecting section 50 (i.e., the Y-direction). The branch vessels 73 can be guided smoothly because the protruding sections 90 are curved (i.e., the inner surfaces of the protruding sections 90 are gradually closer together towards the bottom of the protruding sections 90).

The user can dissect the tissue (fat 74) in the living body and can easily capture the branch vessels 73 embedded in the tissue when the user inserts the second dissecting device 14 into the living body along the blood vessel 72 because the dissecting member 46 of the second dissecting device 14 includes the blood vessel guide passage 54. Consequently, the user can easily stanch and cut the captured branch vessel 73, while observing the branch vessel 73 through the imaging device 17 inserted in the insertion lumen 45.

The treating section 60 for stanching and cutting the branch vessel 73 is provided at a proximal portion of the blood vessel guide passage 54 in the second dissecting device 14. This configuration enables the user to perform capture of the branch vessel 73 and the stanching and cutting treatment of the branch vessel 73 through easy operations, by moving the second dissecting device 14 forward and performing an operation for outputting energy to the treating section 60. The treating section 60 does not necessarily need to be provided with the cutting section 64. The user can also cut a branch vessel 73 which has been stanched by the stanching section 62 by use of an appropriate cutting device provided as a separate body from the second dissecting device 14.

The thickness of the dissecting section 50 of the second dissecting device 14 increases in the proximal direction. Tissue in the living body can thus be effectively dissected.

Figure 15A:
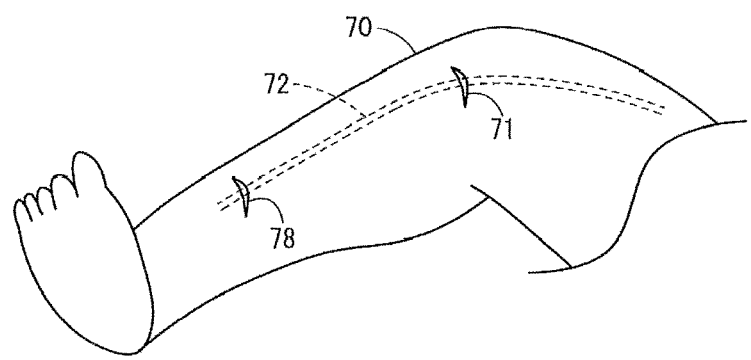
FIG. 15A illustrates cutting of a blood vessel to be harvested.

When the dissecting step has been completed as described above, a cutting step is next conducted. FIG. 15A depicts a cutting step of incising the skin 70 at a position spaced from the incision 71 by a distance corresponding to the length of the blood vessel 72 to be harvested. This second incision 78 and exposes the blood vessel 72 through the incision 78. Both ends of a part of the blood vessel 72 to be harvested are then ligated through the two incisions 71 and 78, after which the blood vessel 72 is cut.

Figure 15B:
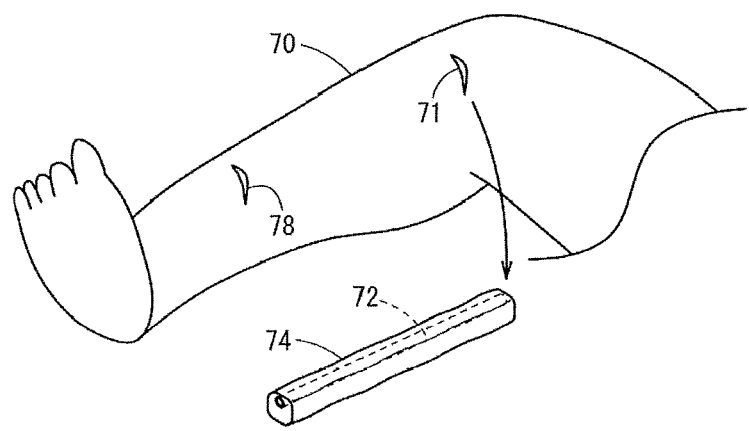
FIG. 15B illustrates extraction of the blood vessel accompanied with fat from the inside of a living body.

After the cutting step is completed, an extracting step is performed. In the extracting step, the blood vessel 72 is taken out of the living body through the incision 71 or the incision 78 along with the accompanying fat 74 as illustrated in FIG. 15B.

The blood vessel 72 and the accompanying fat 74 can thus be harvested from the living body by performing the dissecting, cutting and extracting described above. This method allows the blood vessel 72 to be harvested smoothly and with low invasion. In addition, it is possible to let blood flow in the blood vessel 72 for a prolonged time since the dissecting step can be carried out without cutting the blood vessel 72. Consequently, the blood vessel 72 kept in an ischemic state for a shorter time and accompanied with less damage can be harvested.

A blood vessel 72 covered with the fat 74 is characterized in that lowering of blood flow due to expansion or bending can be inhibited, damage to endotheliocyte, smooth muscle, nutrient vessels (a network of small blood vessels) and the like can be reduced, and thickening of the blood vessel wall can be suppressed. Therefore, the using the blood vessel 72 covered with the fat 74 as a bypass vessel in coronary artery bypass grafting offers an excellent long-term patency rate. Since harvesting the blood vessel 72 accompanied with the fat 74 means that nutrient vessels remain in the blood vessel wall or the fat 74, it is considered that nutrients are supplied to the blood vessel 72 serving as the bypass vessel after bypass grafting, so that the above-mentioned effects are enhanced.

In the description above, the user harvests the blood vessel 72 accompanied with the fat 74 by using the first dissecting device 12 and the second dissecting device 14. However, the blood vessel 72 accompanied with the fat 74 may be harvested by using only the second dissecting device 14 without using the first dissecting device 12. In this case, the above-mentioned operation of inserting and moving forward the second dissecting device 14 is repeated (i.e., performed a plurality of times). The fat 74 can thus be dissected over the whole circumferential range of the perimeter of the blood vessel 72. The distal projections 94 provided at the distal ends of the protruding sections 90 serve as starting points of dissection of the fat 74 in the living body, and, accordingly, the fat 74 can be dissected easily.

The order in which the first dissecting device 12 and the second dissecting device 14 are used may also be reversed from that in the above description. Specifically, a sequence may be adopted in which the second dissecting device 14 is first inserted into the living body and moved forward along the blood vessel 72, then the second dissecting device 14 is withdrawn out of the living body, and thereafter the first dissecting device 12 is inserted into the living body and moved forward along the blood vessel 72.

The second incision 78 may be formed simultaneously with the first incision 71. Alternatively, the second incision 78 may be formed after the first device (the first dissecting device 12, in the case of using the first dissecting device 12 and the second dissecting device 14 in that order) is inserted into the living body (in the period until the insertion of the second dissecting device into the living body).

The first device may be taken out via the second incision 78 in the dissecting step. The second device (the second dissecting device 14, in the case of using the first dissecting device 12 and the second dissecting device 14 in this order) may also be inserted by way of the second incision 78.

A tape, cord, string or the like may be attached to the first dissecting device 12 (for example, to the dissecting member 18) as a mark member for indicating the track (moving path) of the dissecting member 18. This marker allows the fat dissection part in the living body along which the dissection of the first dissecting device 12 has been conducted (track) to be seen. The mark member is configured to be detachable from the first dissecting device 12.

When the first dissecting device 12 with the mark member attached is moved forward within the living body along the blood vessel 72 and the fat 74 is thereby dissected, the mark member is disposed along the fat dissection part in the living body. The mark member is then detached from the first dissecting device 12, after which the first dissecting device 12 is withdrawn out of the living body. The second dissecting device 14 is next moved forward within the living body along the blood vessel 72, to dissect the fat 74. Since the mark member is disposed along the (already formed) fat dissection part, the user can visually confirm the mark member in the living body by the imaging device 17 inserted in the second dissecting device 14. The user can thus easily perform an operation of moving the second dissecting device 14 forward. Note that the mark member is recovered from within the living body after the operation of moving the second dissecting device 14 forward.

In the case of the method wherein the above-mentioned mark member is disposed in the living body, the position of the mark member may be shifted. In view of this possibility, a mark forming mechanism for forming a mark on the dissection interface of the fat 74 at the time of dissecting the fat 74 by the first dissecting device 12 may be provided, in place of attaching the mark member to the first dissecting device 12. Examples of the mark forming mechanism applicable here include a coloring section (pen, etc.) for applying a coloring agent (food red, etc.) to the dissection interface of the fat, and a cauterizing section (electrodes) for cauterizing and browning the dissection interface of the fat. Since such a mark is fixed to the dissection interface of the fat, the user can easily grasp twisting of the blood vessel accompanied with the fat, after the harvesting.

When the second dissecting device 14 and the first dissecting device 12 are used in this order (i.e., the second dissecting device 14 is inserted first into the living body) in dissecting the fat 74 in the living body, the above-mentioned mark member or mark forming mechanism may be provided on the second dissecting device 14.

The detailed description above describes a dissecting device, dissecting system and dissecting method. The invention is not limited, however, to the precise embodiments and variations described. Various changes, modifications and equivalents can be effected by one skilled in the art without departing from the spirit and scope of the invention as defined in the accompanying claims. It is expressly intended that all such changes, modifications and equivalents which fall within the scope of the claims are embraced by the claims.

What is claimed is:

1. A dissecting system comprising:
    a first dissecting device insertable into a living body and movable along a blood vessel, the first dissecting device comprising:
        a first dissecting member configured to dissect tissue surrounding the blood vessel in the living body when the first dissecting member moves forward along the blood vessel in the living body, the first dissecting member comprising a first dissecting section, two second dissecting sections, and a first treating section,
        the first dissecting section extending in an axial direction and possessing a thickness direction and a width direction, the first dissecting section possessing a first lateral side and a second lateral side opposite the first lateral surface in the width direction,
        one of the two second dissecting sections protruding downward in the thickness direction of the first dissecting section from the first lateral side of the first dissecting section and an other of the two second dissecting sections protruding downward in the thickness direction of the first dissecting section from the second lateral side of the first dissecting section, the two second dissecting sections comprising first guide sections configured to guide a branch vessel branched from the blood vessel to the first treating section, and
        the first treating section being configured to perform a predetermined treatment of the branch vessel when the first guide sections guide the branch vessel to the first treating section; and
    a second dissecting device insertable into the living body and movable along the blood vessel, the second dissecting device comprising:
        a second dissecting member configured to dissect the tissue surrounding the blood vessel in the living body when the second dissecting member moves forward along the blood vessel in the living body, the second dissecting member comprising a dissecting section, two protruding sections, and a second treating section,
        the two protruding sections protruding upward in the thickness direction of the dissecting section from both sides of the dissecting section in the width direction, the two protruding sections comprising second guide sections configured to guide the branch vessel to the second treating section, and
        the second treating section configured to perform the predetermined treatment of the branch vessel.

2. The dissecting system according to claim 1, wherein the blood vessel possesses a radial direction;
    a capture range is a range in the radial direction within which capture of the branch vessel is possible; and
    when the tissue is dissected by the first dissecting device with the first dissecting section and the tissue is dissected by the second dissecting device with the dissecting section disposed diametrically opposite the first dissecting device in the radial direction of the blood vessel, the capture range of the first dissecting member overlaps the capture range of the second dissecting member in the radial direction of the blood vessel.

3. The dissecting system according to claim 1, wherein when the first dissecting device is moved forward along the blood vessel for a length to dissect the tissue along a first path and the second dissecting device is moved forward along the blood vessel for the length to dissect the tissue along a second path, the first path of the first dissecting device does not overlap the second path of the second dissecting device.

4. The dissecting system according to claim 1, wherein the first dissecting member possesses a first lateral side and a second lateral side opposite the first lateral side in the width direction;
    the first treating section comprises two treating sections, one of the two treating sections being at the first lateral side of the first dissecting member and an other of the two treating sections being at the second lateral side of the first dissecting; and the second treating section is positioned at a center of the second dissecting device in the width direction.

5. The dissecting system according to claim 4, wherein
the two treating sections of the first treating section each comprise two electrodes and a cutting section,
the second treating section comprises two electrodes and a cutting section, and
the two electrodes of the two treating sections of the first treating section and the two electrodes of the second treating section being configured to stanch the branch vessel, and the cutting section of the two treating sections of the first treating section and the cutting section of the second treating section being configured to cut the branch vessel.

6. A dissecting method for dissecting tissue surrounding a blood vessel in a living body using a dissecting device, the method comprising:
introducing the dissecting device into the living body by way of an incision, the dissecting device comprising a main body and two protruding portions, the main body possessing a thickness direction, the two protruding portions protruding beyond the main body in the thickness direction of the main body in a first direction during the introducing of the dissecting device into the living body;
rotating the dissecting device to a rotated position while the dissecting device is in the living body so that the protruding portions protrude beyond the main body in the thickness direction of the main body in a second direction, the second direction being diametrically opposite the first direction;
dissecting the tissue surrounding the blood vessel in the living body by moving the dissecting device forward along the blood vessel while the dissecting device is in the rotated position;
stanching a branch vessel branched from the blood vessel while dissecting the tissue surrounding the blood vessel in the living body by moving the dissecting device forward along the blood vessel;
cutting the branch vessel of the blood vessel after the branch vessel has been stanched, the cutting occurring while the dissecting device moves forward along the blood vessel to dissect the tissue;
inserting a different dissecting device into the living body before the dissecting device is introduced into the living body, the different dissecting device being configured differently than the dissecting device;
dissecting the tissue surrounding the blood vessel in the living body by moving the different dissecting device forward along the blood vessel by a predetermined length; and
removing the different dissecting device from the living body after the different dissecting device has been moved along the blood vessel by a predetermined distance,
wherein the moving of the dissecting device forward along the blood vessel to dissect the tissue is performed for the predetermined distance.

7. The dissecting method according to claim 6, wherein
the blood vessel possesses a radial direction,
the moving of the dissecting device to dissect the tissue is along a first path,
the moving of the second dissecting device to dissect the tissue is along a second path, and
the first path is diametrically opposite the second path in the radial direction of the blood vessel.

* * * * *